(12) United States Patent
Worrell et al.

(10) Patent No.: US 9,220,559 B2
(45) Date of Patent: Dec. 29, 2015

(54) ARTICULATION JOINT FEATURES FOR ARTICULATING SURGICAL DEVICE

(75) Inventors: Barry C. Worrell, Centerville, OH (US); Sean P. Conlon, Loveland, OH (US); Gary W. Knight, West Chester, OH (US); Matthew C. Miller, Cincinnati, OH (US); Charles J. Scheib, Loveland, OH (US); Frederick E. Shelton, IV, Hillsboro, OH (US); Geoffrey S. Strobl, Williamsburg, OH (US); Jeffrey S. Swayze, Hamilton, OH (US); Aaron C. Voegele, Loveland, OH (US); Charles S. Black, Cincinnati, OH (US); Kreena R. Modi, Akron, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 821 days.

(21) Appl. No.: 13/235,683

(22) Filed: Sep. 19, 2011

(65) Prior Publication Data
US 2012/0078248 A1 Mar. 29, 2012

Related U.S. Application Data

(60) Provisional application No. 61/386,117, filed on Sep. 24, 2010.

(51) Int. Cl.
*A61B 18/14* (2006.01)
*A61B 18/00* (2006.01)

(52) U.S. Cl.
CPC ..... *A61B 18/1445* (2013.01); *A61B 2018/0063* (2013.01); *A61B 2018/00601* (2013.01); *A61B 2018/1455* (2013.01)

(58) Field of Classification Search
USPC .................. 606/51, 52, 129, 130, 205, 34, 41
See application file for complete search history.

(56) References Cited

U.S. PATENT DOCUMENTS

| 2,715,341 A | 8/1955 | Hogan |
| 2,818,744 A | 1/1958 | Moody |

(Continued)

FOREIGN PATENT DOCUMENTS

| DE | 43 00 307 | 7/1994 |
| EP | 1637086 | 3/2006 |

(Continued)

OTHER PUBLICATIONS

International Search Report and Written Opinion dated Feb. 1, 2012 for Application No. PCT/US2011/052723.
International Search Report dated Mar. 19, 2012 for Application No. PCT/US2011/053028.
Office Action Non Final dated Jun. 11, 2014 for U.S. Appl. No. 13/235,660.

(Continued)

*Primary Examiner* — Allen Porter, Jr.
(74) *Attorney, Agent, or Firm* — Frost Brown Todd LLC

(57) ABSTRACT

An electrosurgical device comprises a body, an end effector, a cutting member, and a shaft extending between the body and the end effector. The end effector includes a pair of jaws and at least one electrode operable to deliver RF energy to tissue clamped between the jaws. The cutting member is operable to cut tissue clamped between the jaws. The shaft includes an articulation section that is operable to selectively position the end effector at non-parallel positions relative to the longitudinal axis of the shaft. The articulation section may include beads, segments, asymmetric features, preformedly bent features, an integral hinge, a helical cutout or spring, clevis features, an angled joint, a beaded actuation linkage, and/or an offset pivot, among other things. The device may also include a crimped cutting member, a retroacting cutting member, dual pivoting jaws, and/or a wire tensioning assembly.

12 Claims, 33 Drawing Sheets

(56) References Cited

U.S. PATENT DOCUMENTS

| | | |
|---|---|---|
| 2,857,776 A | 10/1958 | Williams |
| 2,881,645 A | 4/1959 | Kruchten |
| 3,194,530 A | 7/1965 | Heyl |
| 4,203,430 A | 5/1980 | Takahashi |
| 4,483,562 A | 11/1984 | Schoolman |
| 4,723,936 A | 2/1988 | Buchbinder et al. |
| 4,880,015 A | 11/1989 | Nieman |
| 4,945,920 A | 8/1990 | Clossick |
| 5,020,514 A | 6/1991 | Heckele |
| 5,125,895 A | 6/1992 | Buchbinder et al. |
| 5,330,502 A | 7/1994 | Hassler et al. |
| 5,383,888 A | 1/1995 | Zvenyatsky et al. |
| 5,391,180 A | 2/1995 | Tovey et al. |
| 5,395,329 A | 3/1995 | Fleischhacker et al. |
| 5,411,519 A | 5/1995 | Tovey et al. |
| 5,441,499 A | 8/1995 | Fritzsch |
| 5,454,827 A | 10/1995 | Aust et al. |
| 5,462,546 A | 10/1995 | Rydell |
| 5,514,130 A | 5/1996 | Baker |
| 5,514,157 A | 5/1996 | Nicholas et al. |
| 5,540,685 A | 7/1996 | Parins et al. |
| 5,549,637 A | 8/1996 | Crainich |
| 5,562,682 A | 10/1996 | Oberlin et al. |
| 5,607,450 A | 3/1997 | Zvenyatsky et al. |
| 5,609,601 A | 3/1997 | Kolesa et al. |
| 5,632,432 A | 5/1997 | Schulze et al. |
| 5,643,294 A | 7/1997 | Tovey et al. |
| 5,673,840 A | 10/1997 | Schulze et al. |
| 5,700,275 A | 12/1997 | Bell et al. |
| 5,743,456 A | 4/1998 | Jones et al. |
| 5,766,196 A | 6/1998 | Griffiths |
| 5,766,205 A | 6/1998 | Zvenyatsky et al. |
| 5,782,859 A | 7/1998 | Nicholas et al. |
| 5,921,956 A | 7/1999 | Grinberg et al. |
| 5,931,832 A | 8/1999 | Jensen |
| 6,162,208 A | 12/2000 | Hipps |
| 6,179,809 B1 | 1/2001 | Khairkhahan et al. |
| 6,423,059 B1 | 7/2002 | Hanson et al. |
| 6,500,176 B1 | 12/2002 | Truckai et al. |
| 6,554,794 B1 | 4/2003 | Mueller et al. |
| RE38,335 E | 11/2003 | Aust et al. |
| 6,656,177 B2 | 12/2003 | Truckai et al. |
| 6,783,524 B2 | 8/2004 | Anderson et al. |
| 6,817,974 B2 | 11/2004 | Cooper et al. |
| 6,991,627 B2 | 1/2006 | Madhani et al. |
| 7,004,938 B2 | 2/2006 | Ormsby et al. |
| 7,070,595 B2 | 7/2006 | Ormsby et al. |
| 7,081,114 B2 | 7/2006 | Rashidi |
| 7,083,620 B2 | 8/2006 | Jahns et al. |
| 7,087,071 B2 | 8/2006 | Nicholas et al. |
| 7,112,201 B2 | 9/2006 | Truckai et al. |
| 7,125,409 B2 | 10/2006 | Truckai et al. |
| 7,141,897 B2 | 11/2006 | Park |
| 7,150,749 B2 | 12/2006 | Dycus et al. |
| 7,156,846 B2 | 1/2007 | Dycus et al. |
| 7,159,750 B2 | 1/2007 | Racenet et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,208,005 B2 | 4/2007 | Frecker et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,424,965 B2 | 9/2008 | Racenet et al. |
| 7,434,716 B2 | 10/2008 | Viola |
| 7,455,208 B2 | 11/2008 | Wales et al. |
| 7,481,348 B2 | 1/2009 | Marczyk |
| 7,494,039 B2 | 2/2009 | Racenet et al. |
| 7,506,790 B2 | 3/2009 | Shelton, IV |
| 7,540,872 B2 | 6/2009 | Schechter et al. |
| 7,549,564 B2 | 6/2009 | Boudreaux |
| 7,553,275 B2 | 6/2009 | Padget et al. |
| 7,559,450 B2 | 7/2009 | Wales et al. |
| 7,584,880 B2 | 9/2009 | Racenet et al. |
| 7,594,913 B2 | 9/2009 | Ormsby et al. |
| 7,597,230 B2 | 10/2009 | Racenet et al. |
| 7,608,083 B2 | 10/2009 | Lee et al. |
| 7,615,044 B2 | 11/2009 | Scheibe et al. |
| 7,651,494 B2 | 1/2010 | McClurken et al. |
| 7,654,431 B2 | 2/2010 | Hueil et al. |
| 7,691,095 B2 | 4/2010 | Bednarek et al. |
| 7,703,653 B2 | 4/2010 | Shah et al. |
| 7,708,182 B2 | 5/2010 | Viola |
| 7,721,935 B2 | 5/2010 | Racenet et al. |
| 7,771,425 B2 | 8/2010 | Dycus et al. |
| 7,780,054 B2 | 8/2010 | Wales |
| 7,784,662 B2 | 8/2010 | Wales et al. |
| 7,793,814 B2 | 9/2010 | Racenet et al. |
| 7,798,386 B2 | 9/2010 | Schall et al. |
| 7,799,028 B2 | 9/2010 | Schechter et al. |
| 7,815,090 B2 | 10/2010 | Marczyk |
| 7,815,091 B2 | 10/2010 | Marczyk |
| 7,815,637 B2 | 10/2010 | Ormsby et al. |
| 7,828,725 B2 | 11/2010 | Maruyama |
| 7,909,220 B2 | 3/2011 | Viola |
| 8,033,441 B2 | 10/2011 | Marczyk |
| 8,062,306 B2 | 11/2011 | Nobis et al. |
| 8,092,451 B2 | 1/2012 | Schechter et al. |
| 8,100,309 B2 | 1/2012 | Marczyk |
| 8,142,473 B2 | 3/2012 | Cunningham |
| 8,152,799 B2 | 4/2012 | Ormsby et al. |
| 8,161,838 B2 | 4/2012 | Duval |
| 8,197,479 B2 | 6/2012 | Olson et al. |
| 8,205,619 B2 | 6/2012 | Shah et al. |
| 8,236,010 B2 | 8/2012 | Ortiz et al. |
| 8,241,320 B2 | 8/2012 | Lyons et al. |
| 8,245,594 B2 | 8/2012 | Rogers et al. |
| 8,292,147 B2 | 10/2012 | Viola |
| 8,292,889 B2 | 10/2012 | Cunningham et al. |
| 8,317,811 B2 | 11/2012 | Laporte Rosello et al. |
| 8,323,239 B2 | 12/2012 | Bednarek et al. |
| 8,323,297 B2 | 12/2012 | Hinman et al. |
| 8,353,902 B2 | 1/2013 | Prakash |
| 8,357,161 B2 | 1/2013 | Mueller |
| 8,361,067 B2 | 1/2013 | Pellegrino et al. |
| 8,366,709 B2 | 2/2013 | Schechter et al. |
| 8,372,064 B2 | 2/2013 | Douglass et al. |
| 8,377,059 B2 | 2/2013 | Deville et al. |
| 8,403,832 B2 | 3/2013 | Cunningham et al. |
| 8,540,711 B2 | 9/2013 | Dycus et al. |
| 8,628,545 B2 | 1/2014 | Cabrera et al. |
| 8,770,459 B2 | 7/2014 | Racenet et al. |
| 2003/0114851 A1* | 6/2003 | Truckai et al. .................. 606/51 |
| 2006/0259785 A1 | 11/2006 | Nicholas et al. |
| 2007/0043353 A1 | 2/2007 | Dycus et al. |
| 2007/0095877 A1 | 5/2007 | Racenet et al. |
| 2007/0175961 A1 | 8/2007 | Shelton et al. |
| 2007/0219550 A1 | 9/2007 | Thompson et al. |
| 2007/0250072 A1 | 10/2007 | Weitzner et al. |
| 2007/0282324 A1 | 12/2007 | Vaska et al. |
| 2008/0161798 A1 | 7/2008 | Podmore et al. |
| 2009/0125019 A1 | 5/2009 | Douglass et al. |
| 2009/0171354 A1* | 7/2009 | Deville et al. .................. 606/51 |
| 2009/0188965 A1 | 7/2009 | Levin et al. |
| 2009/0283568 A1 | 11/2009 | Racenet et al. |
| 2010/0094289 A1 | 4/2010 | Taylor et al. |
| 2010/0179540 A1 | 7/2010 | Marczyk |
| 2010/0179545 A1 | 7/2010 | Twomey |
| 2010/0249759 A1 | 9/2010 | Hinman et al. |
| 2010/0262161 A1 | 10/2010 | Danitz et al. |
| 2010/0298824 A1 | 11/2010 | Rothstein et al. |
| 2011/0009863 A1 | 1/2011 | Marczyk et al. |
| 2011/0028991 A1 | 2/2011 | Ikeda et al. |
| 2011/0087218 A1 | 4/2011 | Boudreaux et al. |
| 2011/0144430 A1 | 6/2011 | Spivey et al. |
| 2011/0184459 A1 | 7/2011 | Malkowski et al. |
| 2011/0213360 A1 | 9/2011 | Cunningham et al. |
| 2011/0213361 A1 | 9/2011 | Cunningham et al. |
| 2011/0213363 A1 | 9/2011 | Cunningham et al. |
| 2011/0230875 A1 | 9/2011 | Walberg et al. |

(56) References Cited

U.S. PATENT DOCUMENTS

| | | |
|---|---|---|
| 2011/0264074 A1 | 10/2011 | Tegg et al. |
| 2011/0282176 A1 | 11/2011 | Tegg |
| 2012/0109186 A1 | 5/2012 | Parrott et al. |
| 2012/0143088 A1 | 6/2012 | Schultz |
| 2012/0179151 A1 | 7/2012 | Mueller |
| 2012/0203169 A1 | 8/2012 | Tegg |
| 2012/0210223 A1 | 8/2012 | Eppolito |
| 2012/0215220 A1 | 8/2012 | Kerver et al. |
| 2012/0253326 A1 | 10/2012 | Kleyman |
| 2012/0265186 A1 | 10/2012 | Burger et al. |
| 2012/0303013 A1 | 11/2012 | Burell et al. |
| 2012/0316560 A1 | 12/2012 | Hassoun |
| 2013/0012929 A1 | 1/2013 | Malkowski |
| 2013/0012986 A1 | 1/2013 | Suzuki |
| 2013/0023868 A1 | 1/2013 | Worrell et al. |
| 2013/0030428 A1 | 1/2013 | Worrell et al. |
| 2013/0032627 A1 | 2/2013 | Viola |
| 2013/0041403 A1 | 2/2013 | Cunningham et al. |
| 2013/0096407 A1 | 4/2013 | Bednarek et al. |
| 2013/0131651 A1 | 5/2013 | Strobl et al. |

FOREIGN PATENT DOCUMENTS

| | | |
|---|---|---|
| EP | 2151204 | 2/2010 |
| FR | 2 915 873 | 11/2008 |
| WO | WO 00/67834 | 11/2000 |
| WO | WO 2008/045348 | 4/2008 |
| WO | WO 2010/104755 | 8/2010 |
| WO | WO 2012/067468 | 5/2012 |
| WO | WO 2012/078951 | 6/2012 |

OTHER PUBLICATIONS

U.S. Appl. No. 61/410,603, filed Nov. 5, 2010.
U.S. Appl. No. 13/151,481, filed Jun. 2, 2011, Yates et al.
U.S. Appl. No. 13/235,623, filed Sep. 19, 2011, Worrell et al.
U.S. Appl. No. 13/235,648, filed Sep. 19, 2011, Worrell et al.
U.S. Appl. No. 13/235,660, filed Sep. 19, 2011, Worrell et al.
International Search Report and Written Opinion dated Jan. 24, 2012 for PCT/US2011/052734.
Abstract and Machine Translation of German Patent No. DE 43 00 307, Jul. 14, 1994.
Abstract and Machine Translation of French Patent No. FR 2 915 873, Nov. 14, 2008.
Australian Examiner's Report dated Jul. 29, 2013 for Application No. AU 2011305403, 3 pages.
Australian Examiner's Report dated Jul. 25, 2013 for Application No. AU 2011305410, 4 pages.
Office Action, Final, dated Nov. 13, 2014 for U.S. Appl. No. 13/235,660, 13 pages.
Office Action, Restriction Requirement, dated Nov. 6, 2014 for U.S. Appl. No. 13/741,650, 7 pages.
Office Action, Non-Final, dated Jan. 30, 2015 for U.S. Appl. No. 13/741,650, 13 pages.
Australian Full Examiner's Report dated Apr. 15, 2015 for Application No. AU 2011305403, 4 pages.
Chinese First Office Action dated Jan. 5, 2015 for Application No. CN 201180046071.X, 8 pages.
Chinese First Office Action dated Dec. 3, 2014 for Application No. CN 201180046162.3, 5 pages.
Office Action, Non-Final, dated Apr. 1, 2015 for U.S. Appl. No. 13/235,660, 16 pages.

* cited by examiner

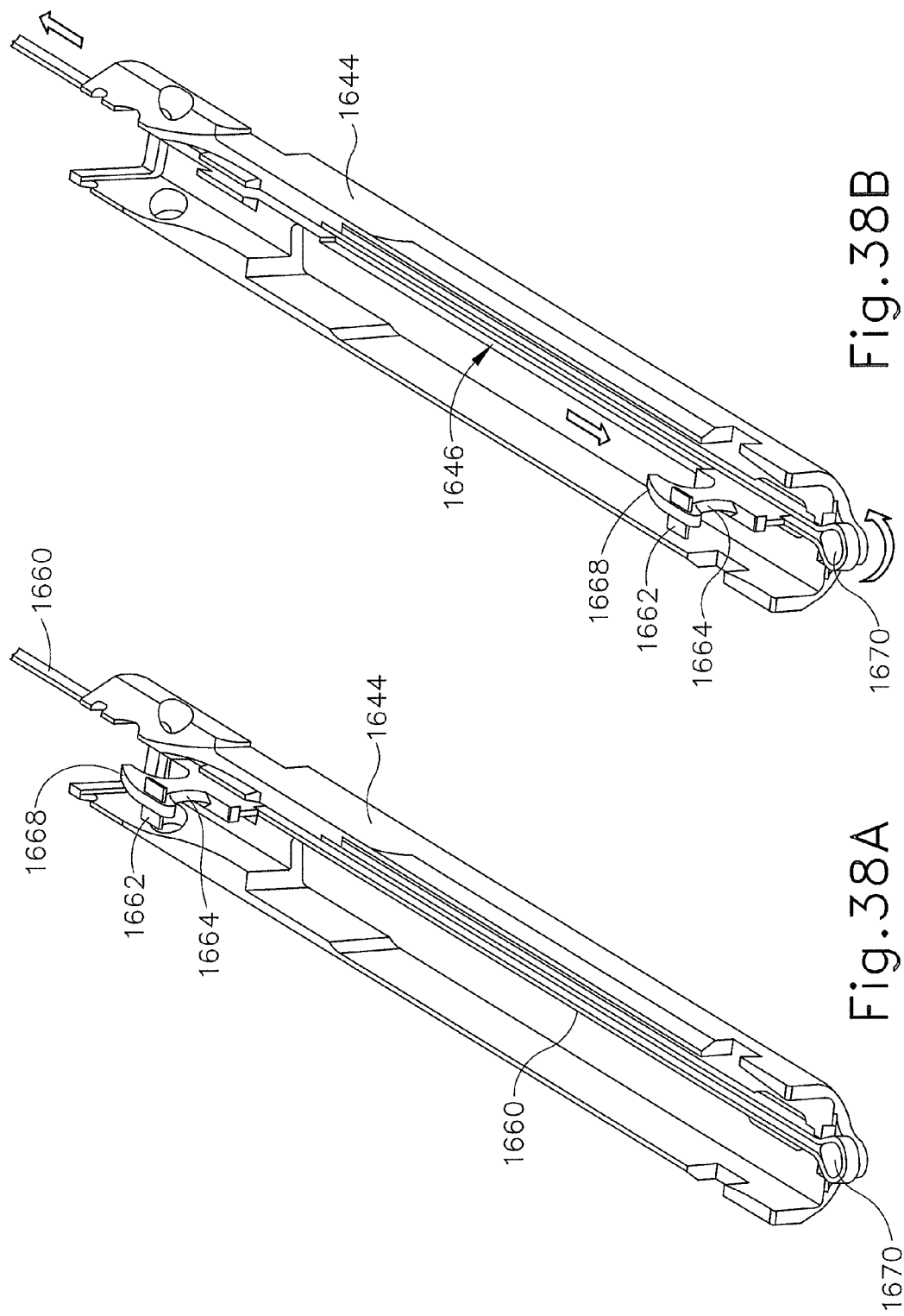

und used, it
ARTICULATION JOINT FEATURES FOR ARTICULATING SURGICAL DEVICE

PRIORITY

This application claims priority to U.S. Provisional Application Ser. No. 61/386,117, filed Sep. 24, 2010, entitled "Articulating Surgical Device," the disclosure of which is incorporated by reference herein.

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, published as U.S. Pub. No. 2012/0116379, now U.S. Pat. No. 9,161,803 issued Oct. 20, 2015, the disclosure of which is incorporated by reference herein.

In addition, a variety of surgical instruments include a shaft having an articulating section, providing enhanced positioning capabilities for an end effector that is located distal to the articulating section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 38A depicts a partial perspective view of an exemplary alternative end effector for incorporation into the device of FIG. 1, with a cutting member positioned at a proximal location;

FIG. 38B depicts a partial perspective view of the end effector of FIG. 38A, with the cutting member positioned at a distal location;

Figure 1:
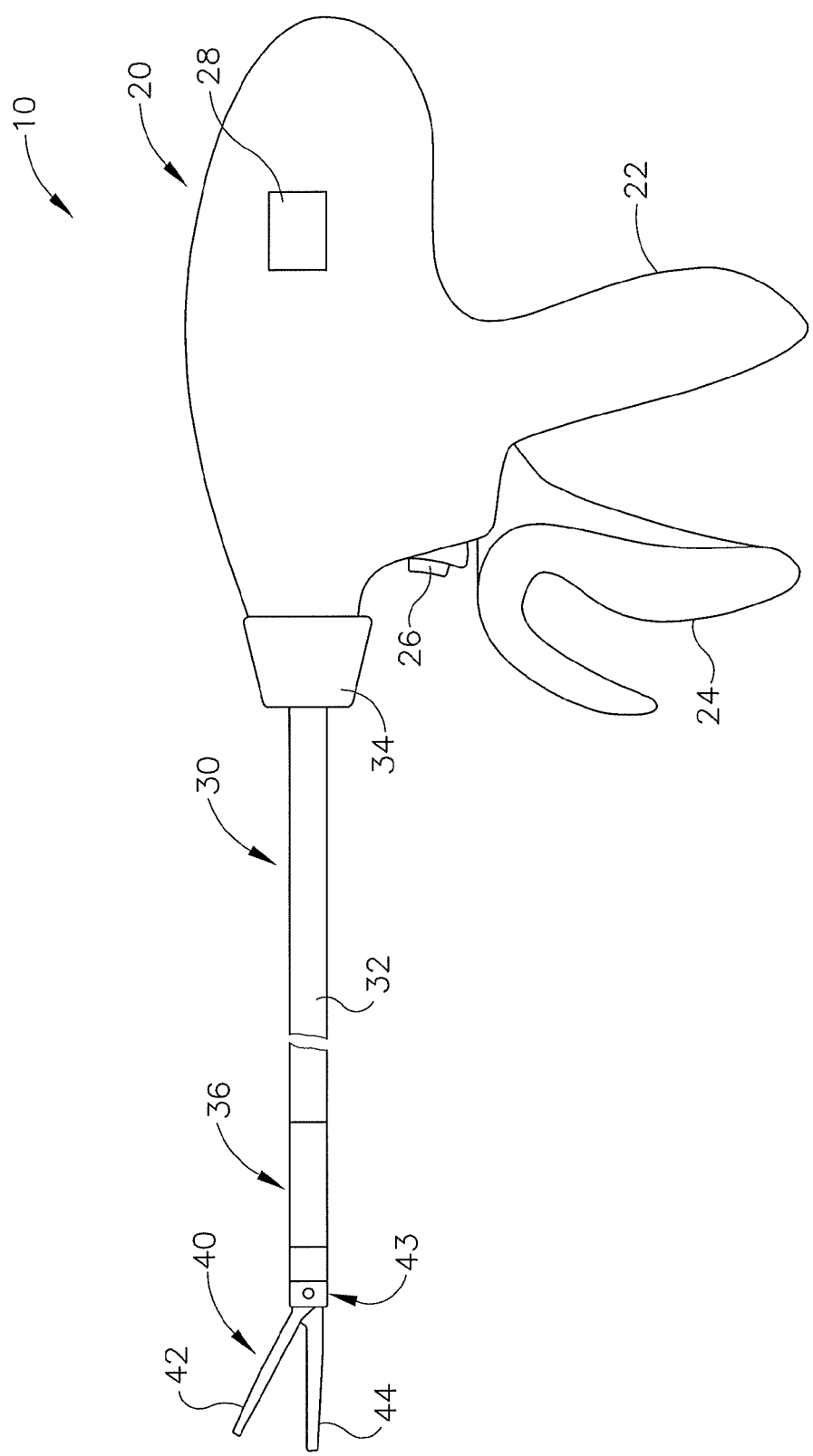
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. Nos. 6,500,176; 7,112,201; 7,125,409; 7,169,146; 7,186,253; 7,189,233; 7,220,951; 7,309,849; 7,311,709; 7,354,440; 7,381,209; U.S. Pub. No. 2011/0087218, now U.S. Pat. No. 8,939,974; and/or U.S. patent application Ser. No. 13/151,481, now U.S. Pat. No. 9,161,803. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. It should be understood that pistol grip (22), trigger (24), and button (26) may be modified, substituted, supplemented, etc. in any suitable way, and that the descriptions of such components herein are merely illustrative. Articulation control (28) of the present example is operable to selectively control articulation section (36) of shaft (30), which will be described in greater detail below. Various examples of forms that articulation control (28) may take will also be described in greater detail below, while further examples will be apparent to those of ordinary skill in the art in view of the teachings herein.

Shaft (30) of the present example includes an outer sheath (32) and an articulating section (36). Articulating section (36) is operable to selectively position end effector (40) at various angles relative to the longitudinal axis defined by sheath (32). Various examples of forms that articulating section (36) and other components of shaft (30) may take will be described in greater detail below, while further examples will be apparent to those of ordinary skill in the art in view of the teachings herein. For instance, it should be understood that various components that are operable to actuate articulating section (36) may extend through the interior of sheath (32). In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulating section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulating section (36). Other suitable rotation schemes will be apparent to those of ordinary skill in the art in view of the teachings herein. Of course, rotatable features may simply be omitted if desired.

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
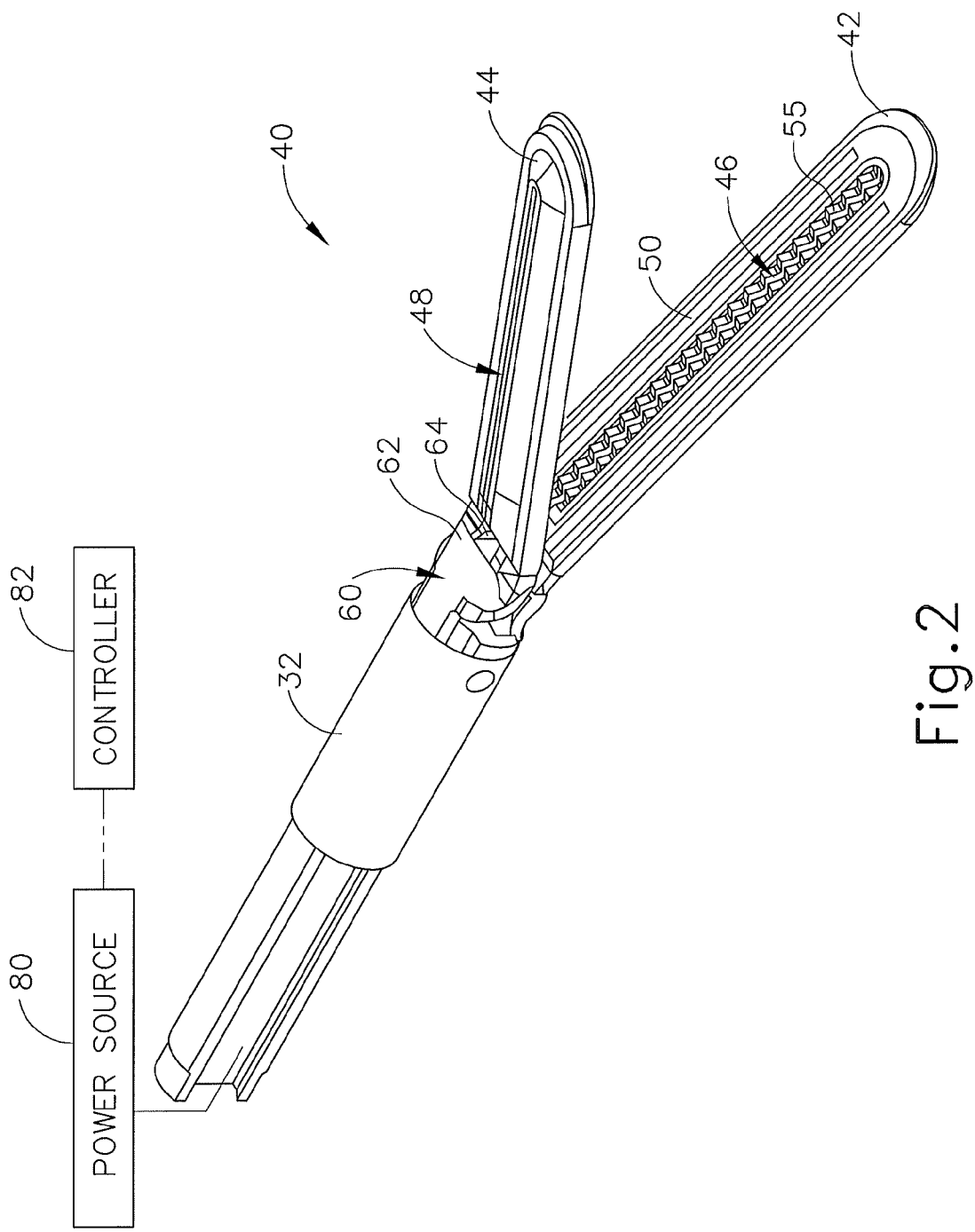
FIG. 2 depicts a perspective view of the end effector of the device of FIG. 1, in an open configuration.
Figure 3:
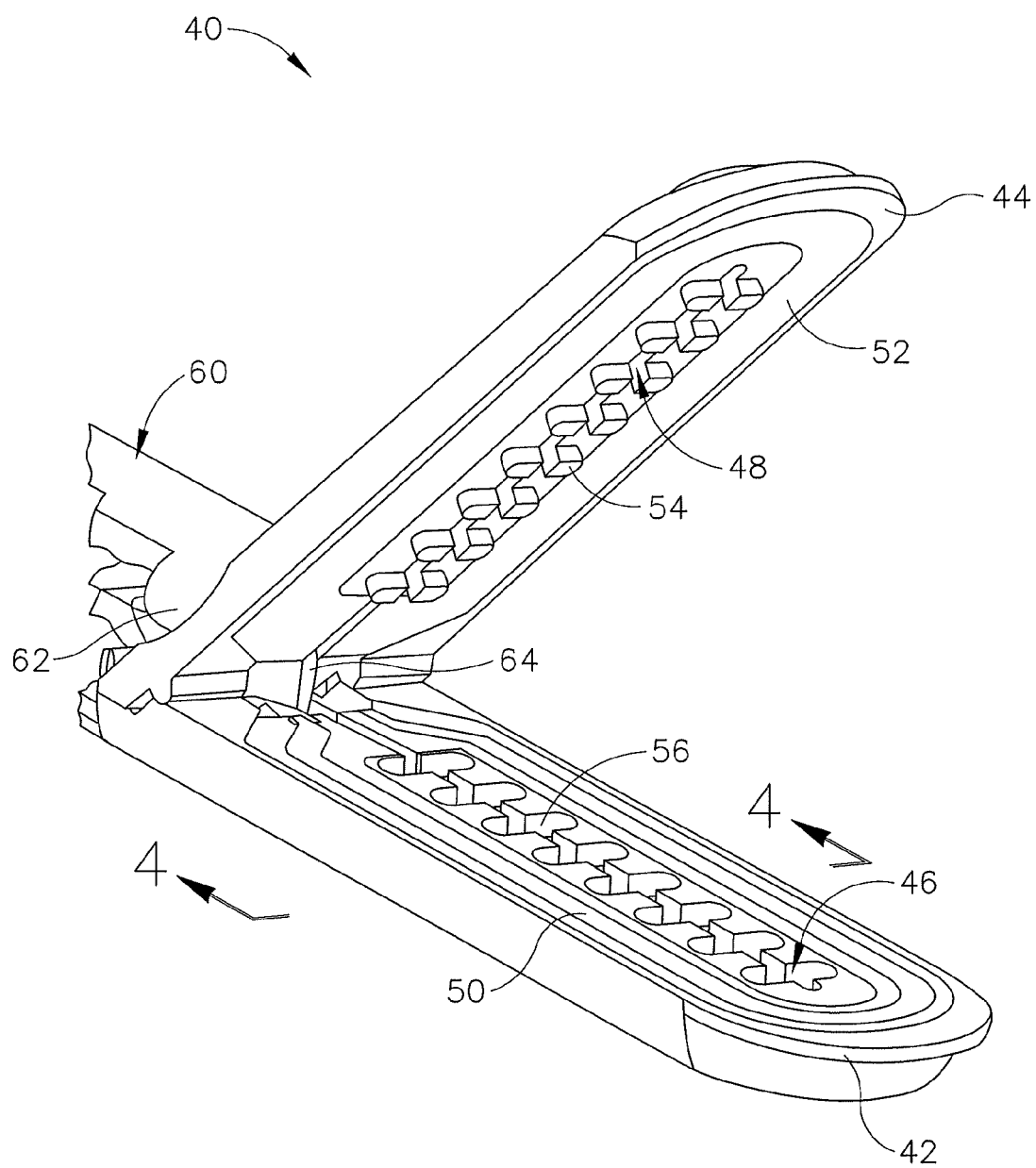
FIG. 3 depicts another perspective view of the end effector of the device of FIG. 1, in an open configuration.
Figure 4:
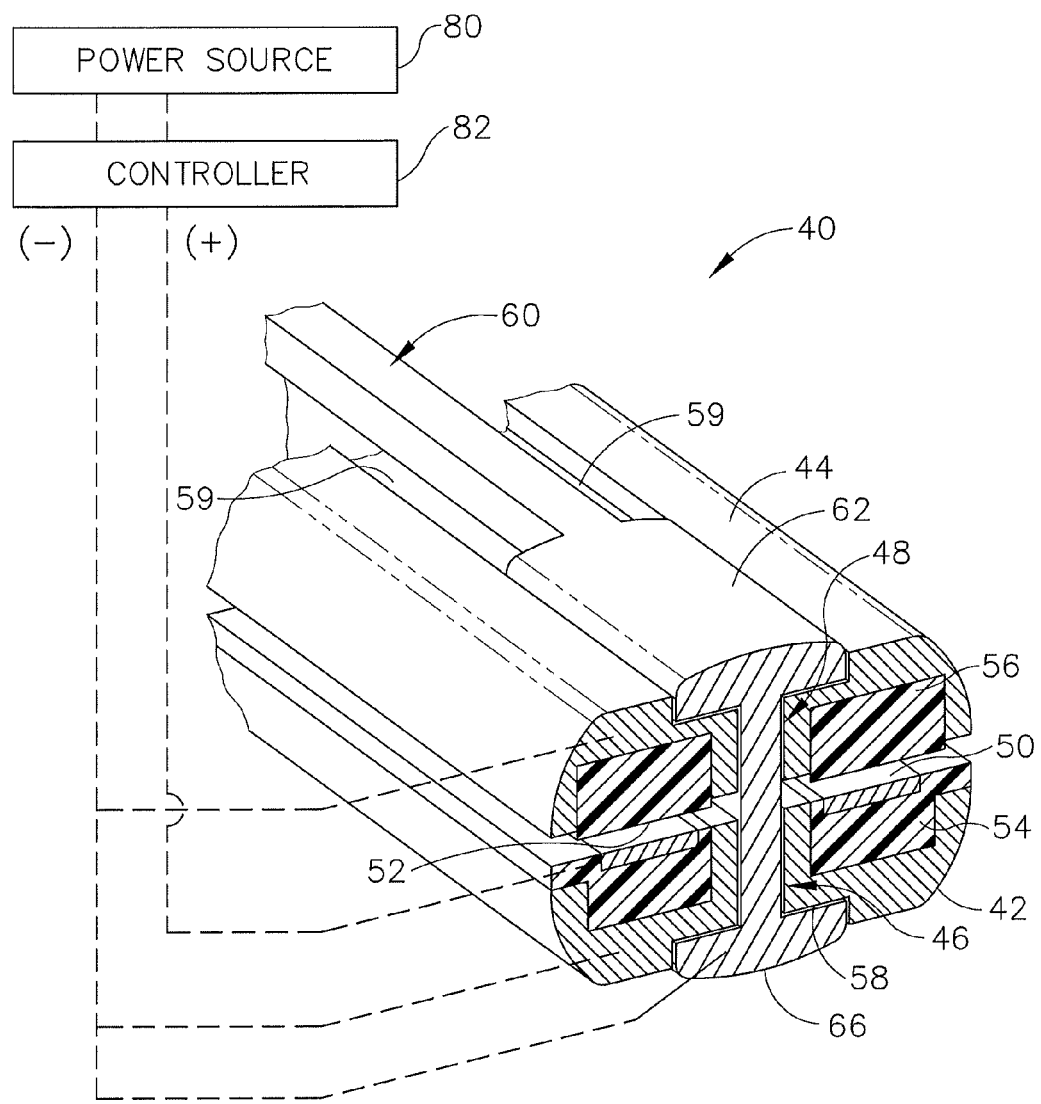
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulating section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG.

4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (44) when firing beam (60) is actuated distally by squeezing trigger (24) toward pistol grip (22).

With tissue layers captured between jaws (42, 44) firing beam (60) continues to advance distally by the user squeezing trigger (24) toward pistol grip (22). As firing beam (60) advances distally, distal blade (64) simultaneously severs the clamped tissue layers, resulting in separated upper layer portions being opposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52).

While several of the teachings below are described as variations to electrosurgical instrument (10), it should be understood that various teachings below may also be incorporated into various other types of devices. By way of example only, in addition to being readily incorporated into electrosurgical instrument (10), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Exemplary Articulation Joint Configurations

As noted above, some versions of shaft (30) include an articulation section (36), which is operable to selectively position end effector (40) at various angles relative to the longitudinal axis defined by sheath (32). Several examples of forms that articulation section (36) and other components of shaft (30) may take will be described in greater detail below, while further examples will be apparent to those of ordinary skill in the art in view of the teachings herein. By way of example only, some merely illustrative alternative examples of articulation section (36) are disclosed in U.S. patent application Ser. No. 13/235,660, entitled "Articulation Joint Features for Articulating Surgical Device," filed on even date herewith, published as U.S. Pub. No. 2012/0078247, the disclosure of which is incorporated by reference herein.

A. Exemplary Articulation Section with Adjacent Beads

Figure 5:
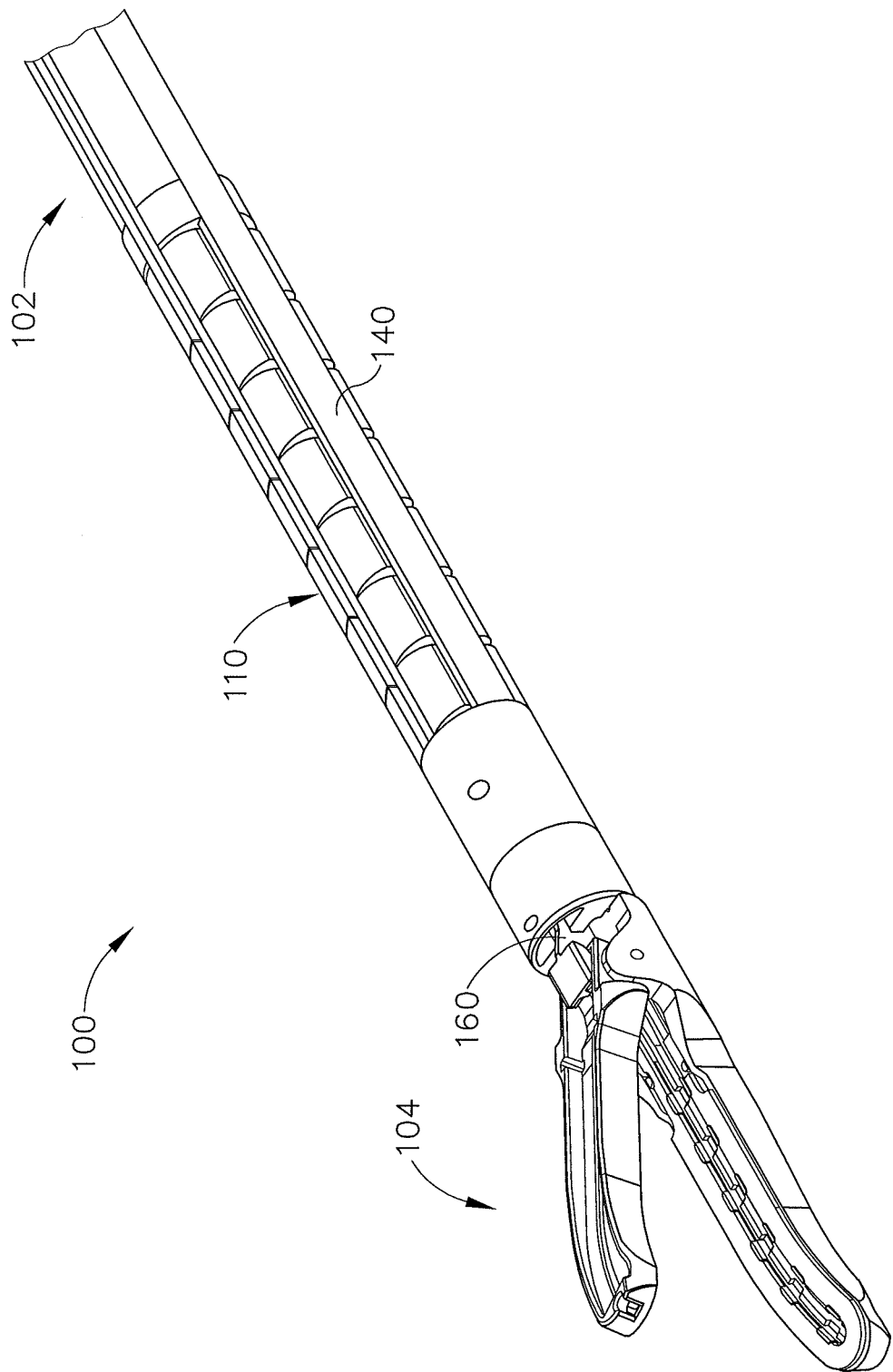
FIG. 5 depicts a perspective view of an exemplary articulation section for the shaft of the device of FIG. 1.
Figure 6:
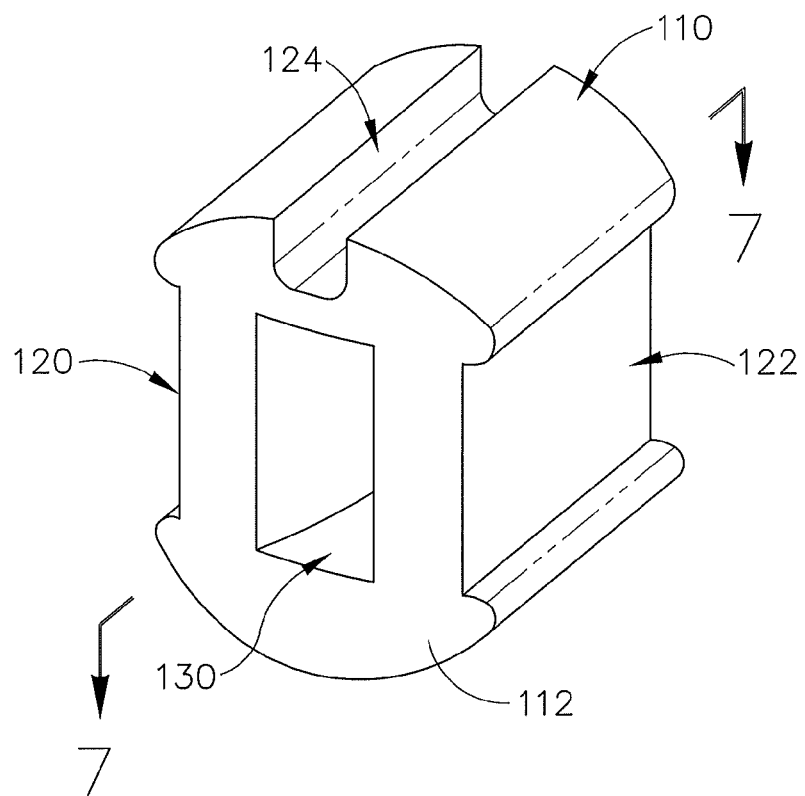
FIG. 6 depicts a perspective view of a bead of the articulation section of FIG. 5.
Figure 7:
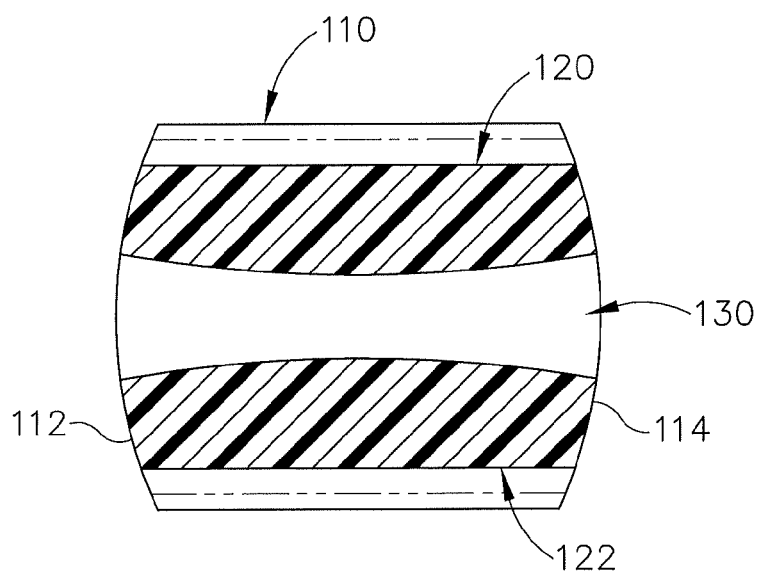
FIG. 7 depicts a cross-sectional view of the bead of FIG. 6, taken along line 7-7 of FIG. 6.

FIG. 5 shows an exemplary articulation section (100) disposed between a rigid shaft section (102) and an end effector (104). It should be understood that these features may be readily incorporated into electrosurgical instrument (10) described above, with shaft section (102) corresponding to shaft (30) and end effector (104) corresponding to end effector (40). Articulation section (100) of this example comprises a plurality of coaxially aligned beads (110). As best seen in FIGS. 6-7, each bead (110) includes a first face (112) and a second face (114). Each face (112, 114) has a convex configuration. With beads (110) positioned adjacent to each other, the convex configuration of faces (112, 114) may facilitate articulation of articulation section (100). For instance, the face (112) of one bead (110) may simply roll against the face (114) of an adjacent bead (110) during articulation.

As shown in FIG. 6, the outer perimeter of each bead (110) also includes recesses (120, 122, 124) extending from face (112) to face (114). Beads (110) are all configured similarly in this example, such that corresponding recesses (120, 122, 124) of adjacent beads (110) may be readily aligned with each other. As shown in FIG. 5, recesses (120, 122) receive respective articulation bands (140). The distal ends of articulation bands (140) are secured to the distal end of articulation section (100). The proximal ends of articulation bands (140) are in communication with a control such as articulation control (28). In some versions, articulation control (28) is operable to selectively advance or retract one band (140) while keeping the position of the other band (140) substantially constant, thereby causing articulation section (100) to bend. In some other versions, articulation control (28) is operable to selectively advance one band (140) while simultaneously retracting the other band (140); and/or to selectively retract the band (140) while simultaneously advancing the other band (140). Of course, bands (140) may be substituted with cables and/or various other types of components. A flexible sheath or wrap may be positioned about articulation section (100), to assist in holding bands (140) against molded member (110). In addition or in the alternative, molded member (110) may include vertically extending slots and/or other types of features that hold bands (140) against molded member (110), including when articulation section (100) is in a bent configuration. As yet another merely illustrative example, bands (140) may be exposed and may be free to move laterally away from articulation section (100) during articulation. For instance, when a band (140) is pulled and articulation section (100) bends, the pulled band (140) may tend to remain substantially straight while articulation section bends, producing a bow string type of effect. Allowing this to occur may improve the mechanical advantage of band (140), thereby reducing the articulation load encountered by the user.

Recess (124) is configured to receive a wire (not shown). Such a wire may be configured to provide electrical communication between end effector (104) and a power source. It should be understood that, as with other wires referred to herein, such a wire may readily bend with articulation section (100) when articulation section (100) is articulated. Each bead (110) further includes a central bore (130) extending from face (112) to face (114). Bores (130) of all beads (110) are all substantially coaxially aligned when articulation section (100) is in a substantially straight configuration. It should be understood that firing beam (160) may extend through bores (130). Firing beam (160) is flexible enough to bend and translate along a curved path defined by bores (130) when articulation section (100) is in a bent configuration. Firing beam (160) may thus be used to actuate end effector (104) in the manner described above, regardless of whether articulation section (100) is in a straight configuration or a bent configuration. As best seen in FIG. 7, each bore (130) has an hourglass configuration, which may facilitate flexing of firing beam (160) through articulation section (100) when articulation section (100) is in an articulated configuration. For instance, the hourglass configuration of bores (130) may limit bending stresses on firing beam (160). In addition or in the alternative, the hourglass configuration of bores (130) may limit the buckling space for firing beam (160) when firing beam (160) is under a load (e.g., when firing beam (160) is advancing the knife through tissue while articulation section (100) is in an articulated configuration, etc.).

Figure 8:
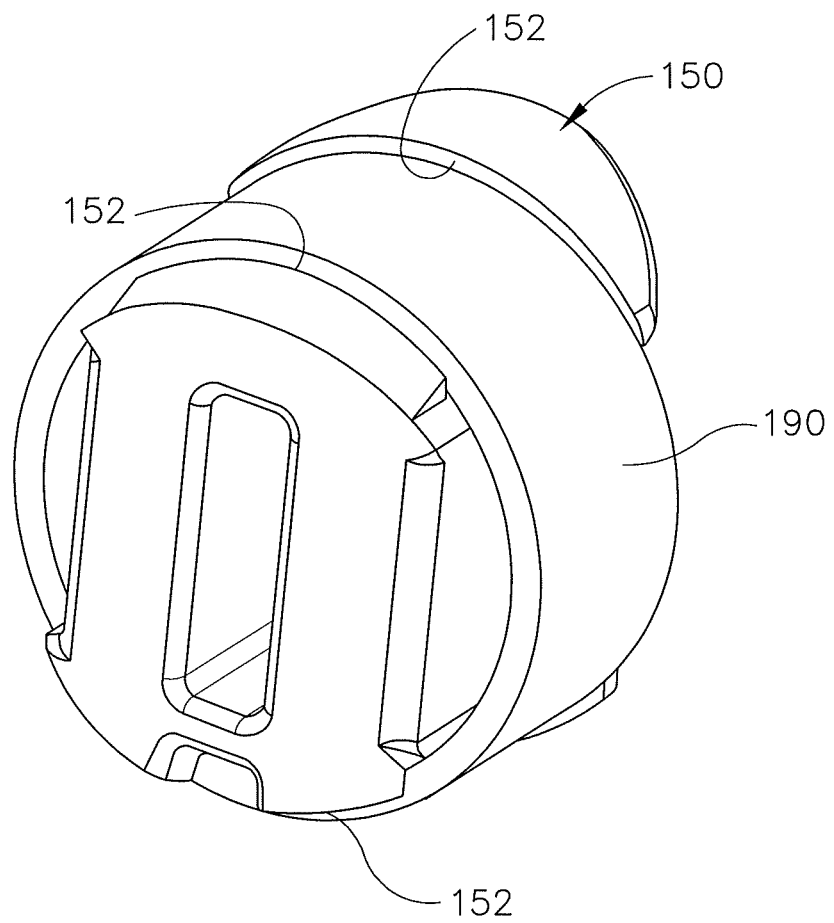
FIG. 8 depicts a perspective view of an exemplary alternative bead for use in the articulation section of FIG. 5.

FIG. 8 shows a merely illustrative variation of bead (110). In particular, FIG. 8 shows an exemplary alternative bead (150) that is configured to receive a cuff (190). One, more than one, or all beads (150) in an articulation section may include a respective cuff (190). Cuff (190) is configured to snap onto bead by engaging with ridges (152) presented by bead (150). Cuff (190) is further configured to substantially retain articulation bands (140) against bead (110) in recesses (120, 122). In addition, cuff (190) is configured to substantially retain a wire in recess (124). Cuffs (190) may also protect tissue that is adjacent to the articulation section, such as by preventing bands (140) from being pulled away from beads (150) and being caught on such tissue. Bead (150) is otherwise configured substantially the same as bead (110) in this example. It should be understood that each bead (150) in an articulation section may have a respective cuff (190). It should also be understood that the presence of cuffs (190) on beads (150) need not interfere with articulation of such an articulation section in any way. Still other suitable variations of beads (110, 150) and other components for articulation section (100) will be apparent to those of ordinary skill in the art in view of the teachings herein. It should also be understood that the number of beads (110, 150) may be increased or decrease to allow for more or less articulation of end effector (104) and/or to adjust stresses on firing beam (160).

B. Exemplary Articulation Section with Interlocked Beads

Figure 9:
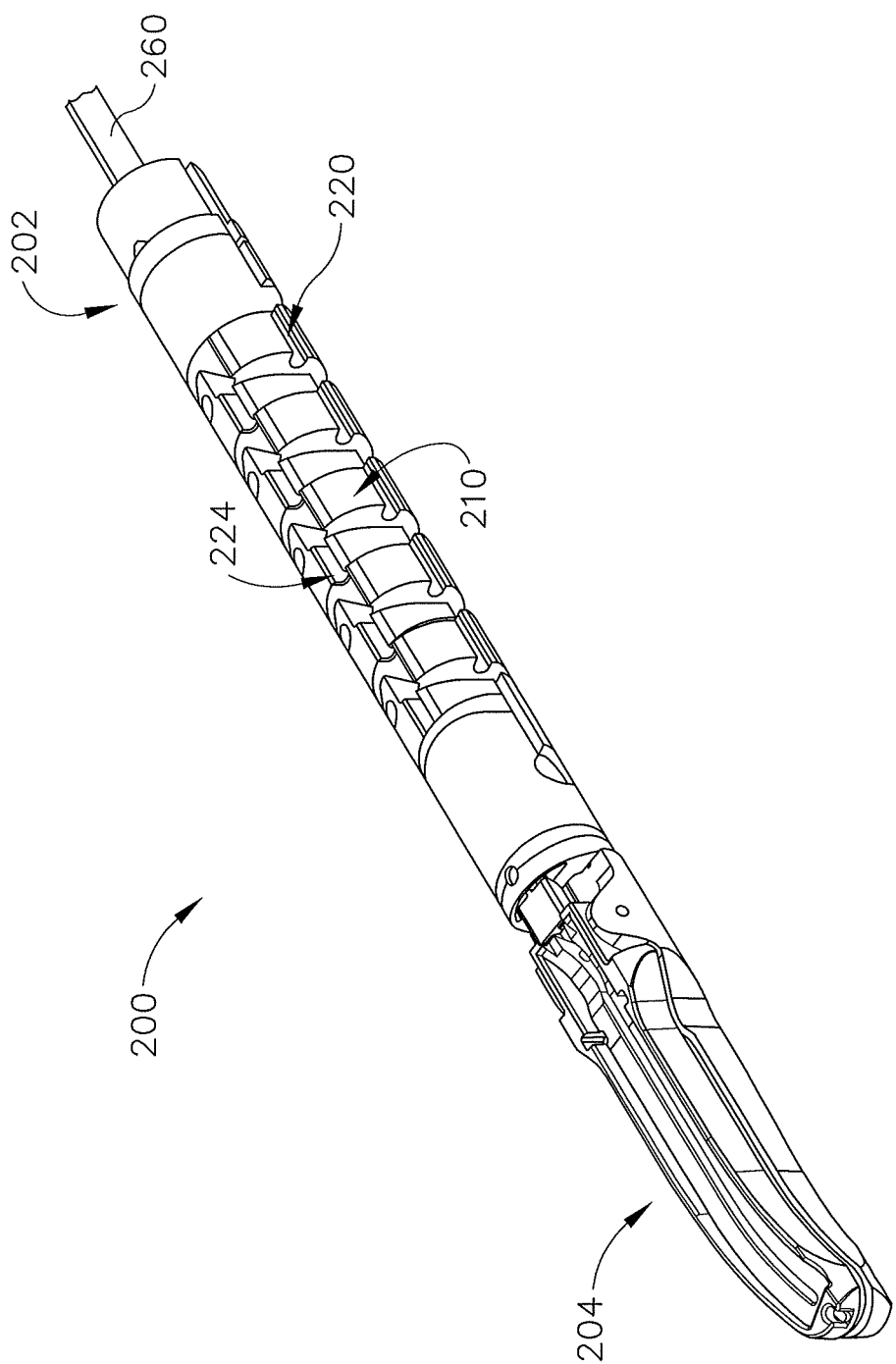
FIG. 9 depicts a perspective top view of another exemplary articulation section for the shaft of the device of FIG. 1.
Figure 10:
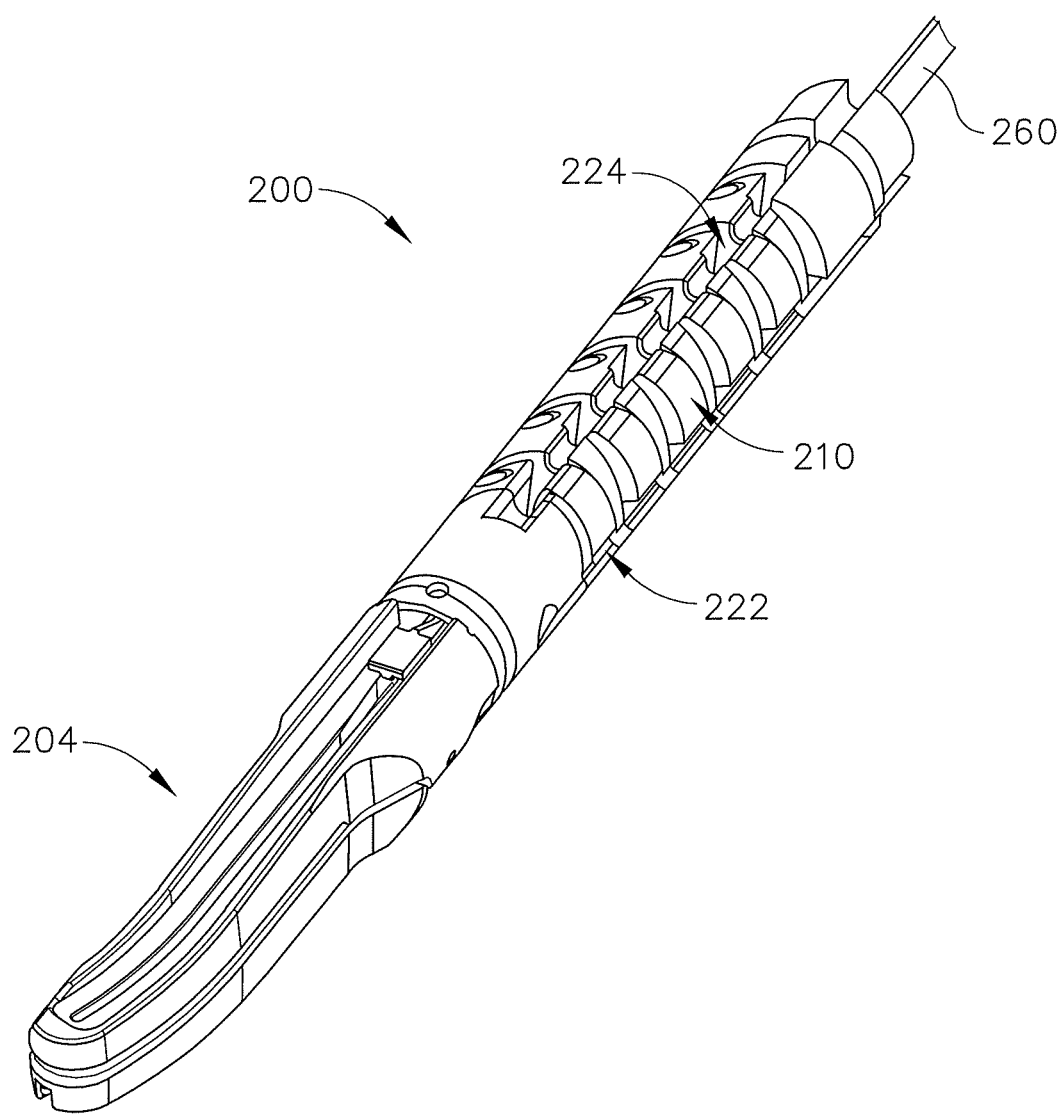
FIG. 10 depicts a perspective bottom view of the articulation section of FIG. 9.
Figure 11:
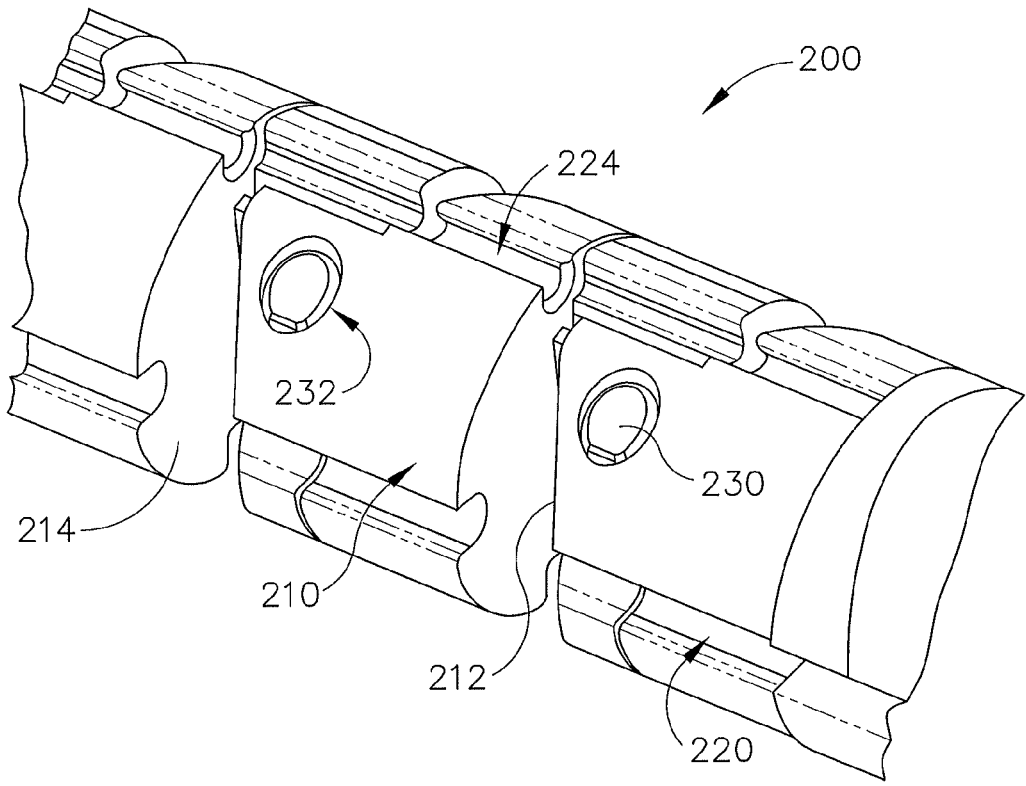
FIG. 11 depicts a partial perspective view of interlocked beads of the articulation section of FIG. 9.
Figure 12:
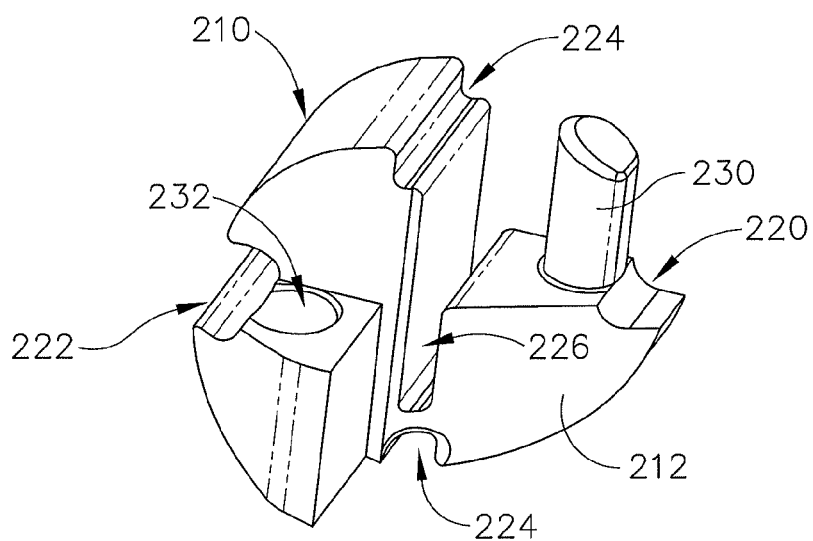
FIG. 12 depicts a perspective view of a bead of the articulation section of FIG. 9.

FIGS. 9-11 show another exemplary articulation section (200) disposed between a rigid shaft section (202) and an end effector (204). It should be understood that these features may be readily incorporated into electrosurgical instrument (10) described above, with shaft section (202) corresponding to shaft (30) and end effector (204) corresponding to end effector (40). Articulation section (200) of this example comprises a plurality of coaxially aligned beads (210). As best seen in FIGS. 11-12, each bead (210) includes a first face (212) and a second face (214). First face (212) is formed at an angle, such that first face (212) is non-parallel to second face (214). Thus, when beads (210) are positioned in a line, the first face (212) of one bead (210) forms a gap with the second face (214) of an adjacent bead (210). These gaps provide clearance for a chain of beads (210) to bend, thereby providing articulation for articulation section (200). Such gaps may also help minimize friction through articulation section (200), thereby facilitating articulation of end effector (204).

Each bead (210) of this example also includes a plurality of recesses (220, 222, 224, 226), a post (230), and a post passage (232). Post (230) may comprise an integrally formed feature of bead (210), an inserted pin, and/or any other suitable structure. Posts (230) and post passages (232) complement each other such that the post (230) of one bead (210) may be inserted into the post passage (232) of another bead (210). An interlocked chain of beads (210) may thus be formed to provide articulation section (200), with cooperating posts (230)

and passages (232) acting as alternatingly offset hinges. It should be understood that beads (210) of this example are configured such that the vertical orientation of each bead (210) in a chain is reversed along the length of a chain. In other words, a first bead (210) may have a first vertical orientation, while the next adjacent bead (210) has an opposite vertical orientation, with the net adjacent bead (210) having the first vertical orientation, etc. It should also be understood that a portion of a bead (210) vertically overlaps a corresponding portion of an adjacent bead (210) in the chain.

When beads (210) are joined together and aligned, recesses (220, 222, 224, 226) align with each other. Recesses (220, 222) are configured to receive respective articulation cables (not shown). Such articulation cables may be operable in a manner similar to that described above for articulation bands (140, 142). In some other versions, recesses (220, 222) are configured to form channels that receive bands instead of cables. Other suitable features that may be used to provide articulation of articulation section (200) will be apparent to those of ordinary skill in the art in view of the teachings herein. Recess (224) is configured to receive a wire (not shown). Such a wire may be configured to provide electrical communication between end effector (204) and a power source. It should be understood that, as with other wires referred to herein, such a wire may readily bend with articulation section (200) when articulation section (200) is articulated.

When beads (210) are joined together, recesses (226) of adjacent beads (210) align and cooperate form a channel through which firing beam (260) is disposed. As with articulation section (100) described above, articulation section (200) may include an external shrink tube, some other type of cover, cuffs for beads (210), etc. Still other suitable variations of beads (210) and other components for articulation section (200) will be apparent to those of ordinary skill in the art in view of the teachings herein. It should also be understood that the number of beads (210) may be increased or decrease to allow for more or less articulation of end effector (204) and/or to adjust stresses on firing beam (260).

C. Exemplary Articulation Section with Interlocking Segments

Figure 13:
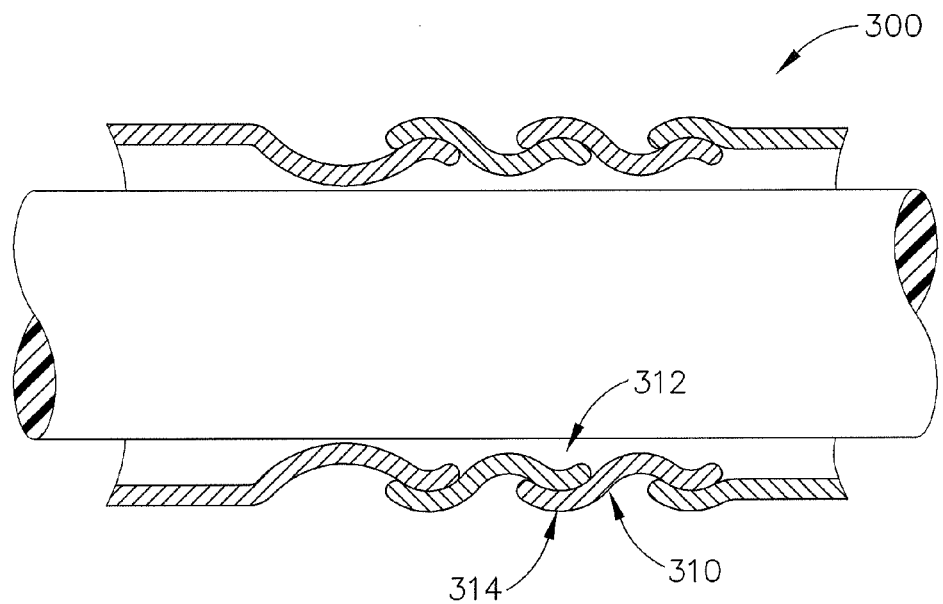
FIG. 13 depicts a partial cross-sectional view of another exemplary articulation section for the shaft of the device of FIG. 1.

FIG. 13 shows another exemplary articulation section (300) that may be positioned between a rigid shaft section (such as any rigid shaft section referred to above) and an end effector (such as any end effector referred to above). It should be understood that these features may be readily incorporated into electrosurgical instrument (10) described above. Articulation section (300) of this example comprises a series of interlocking segments (310), which are collectively configured in a manner similar to armor of an armored cable. Each segment includes a respective distal locking feature (312) and a proximal locking feature (314). The distal locking feature (312) of each segment (310) is configured to engage the proximal locking feature (314) of the adjacent segment (310), such that segments (310) may be snapped together to form articulation section (300).

Segments (310) are configured to selectively move relative to each other when segments are joined together. One or more cables, bands, shafts, etc. may be actuated to bend articulation section (300), such as in accordance with any of the teachings herein. In some versions, pushing or pulling components within articulation section (300) and outside the neutral plane may eventually force segments (310) to become more compact on one side of articulation section (300) and extend on the opposing side of articulation section (300), resulting in a bend. When forced to the extreme position (e.g., the minimum bend radius) in either direction, articulation section (300) may eventually become naturally rigid, due to the configuration of segments (310). The number of segments (310) used in the assembly may determine the maximum resultant angle of articulation section (300). The geometry of segments (310) may determine the bend radius of articulation section (300).

D. Exemplary Articulation Section with Integral Switches

Figure 14:
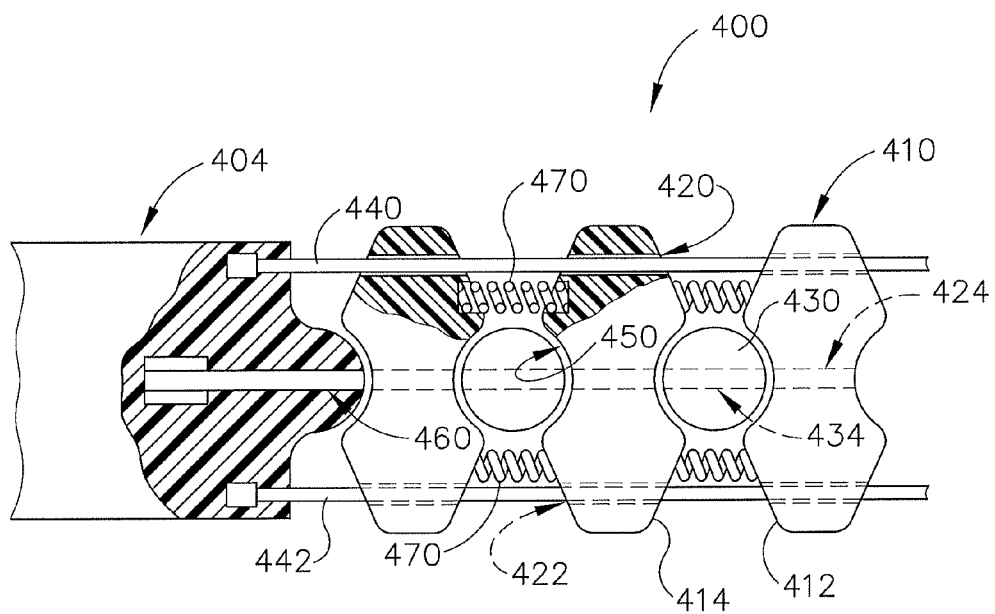
FIG. 14 depicts a partial cross-sectional view of another exemplary articulation section for the shaft of the device of FIG. 1.

FIG. 14 shows another exemplary articulation section (400) that may be positioned between a rigid shaft section (such as any rigid shaft section referred to above) and an end effector (404). It should be understood that these features may be readily incorporated into electrosurgical instrument (10) described above, with end effector (404) corresponding to end effector (40). Articulation section (400) of this example comprises a series of segments (410) and posts (430). Segments (410) each include a first face (412) and a second face (414). Faces (412, 414) are angled to clearance for a series of beads (410) to bend, thereby providing articulation for articulation section (400). Segments (410) also include channels (420, 422) through which articulation cables (440, 442) extend. Such articulation cables (440, 442) may be operable in a manner similar to that described above for articulation bands (140, 142). In some other versions, channels (420, 422) receive bands instead of cables (440, 442). Other suitable features that may be used to provide articulation of articulation section (400) will be apparent to those of ordinary skill in the art in view of the teachings herein.

Segments (410) and posts (430) each also define a firing bar channel (424, 434), through which firing bar (460) extends. In some versions, firing bar channels (424, 434) are electrically insulated. Segments (410) also include conductive recesses (450) that are proximate to posts (430). Posts (430) are also conductive, such that posts (430) and recesses (450) together form a path for electrical continuity through articulation section (400) when all posts (430) of articulation section (400) contact all corresponding recesses (450) of articulation section (400). This electrical path may ultimately couple end effector (404) with a power source.

Pairs of springs (470) are positioned between adjacent segments (410) to resiliently bias segments (410) apart from each other. Thus, springs (470) are configured to encourage a break in the electrical path provided by articulation section (400), even when articulation section (400) is in a bent configuration. However, articulation section (400) is configured such that posts (430) will contact recesses (450) when both cables (440, 442) are pulled simultaneously, overcoming the bias provided by springs (470) to provide electrical continuity through articulation section (400). It should be understood that articulation section (400) may still maintain a bent configuration when cables (440, 442) are pulled simultaneously. Various suitable ways in which cables (440, 442) may be pulled simultaneously will be apparent to those of ordinary skill in the art in view of the teachings herein. It should also be understood that the simultaneous pulling of cables (440, 442) may be mechanically tied to distal advancement of firing bar (460), such that these actions all occur simultaneously. Furthermore, relying on such features to complete a circuit to end effector (404) may eliminate the need for a separate activation button.

Figure 15:
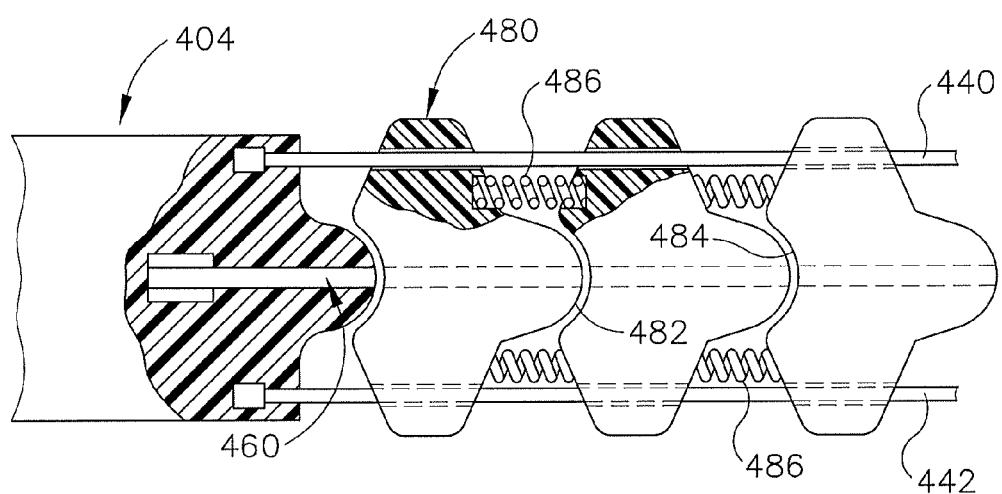
FIG. 15 depicts a partial cross-sectional view of another exemplary articulation section for the shaft of the device of FIG. 1.

FIG. 15 shows an exemplary alternative form of segments (410). In particular, FIG. 15 shows a series of alternative segments (480) that include conductive protrusions (482) to nest in conductive recesses (484) of adjacent segments (480). Protrusions (482) thus serve as a functional substitute for posts (430) in this example. Springs (486) bias segments (480) apart to break electrical continuity through segments (480), though segments (480) may be brought together to establish electrical continuity through segments (480). Segments (480) of this example are thus analogous to segments (410) other than the substitution of protrusions (482) for posts (430). Still other suitable variations for segments (410, 480) and other components of articulation section (400) will be apparent to those of ordinary skill in the art in view of the teachings herein.

E. Exemplary Articulation Section with Single Sided Articulation

Figure 16:
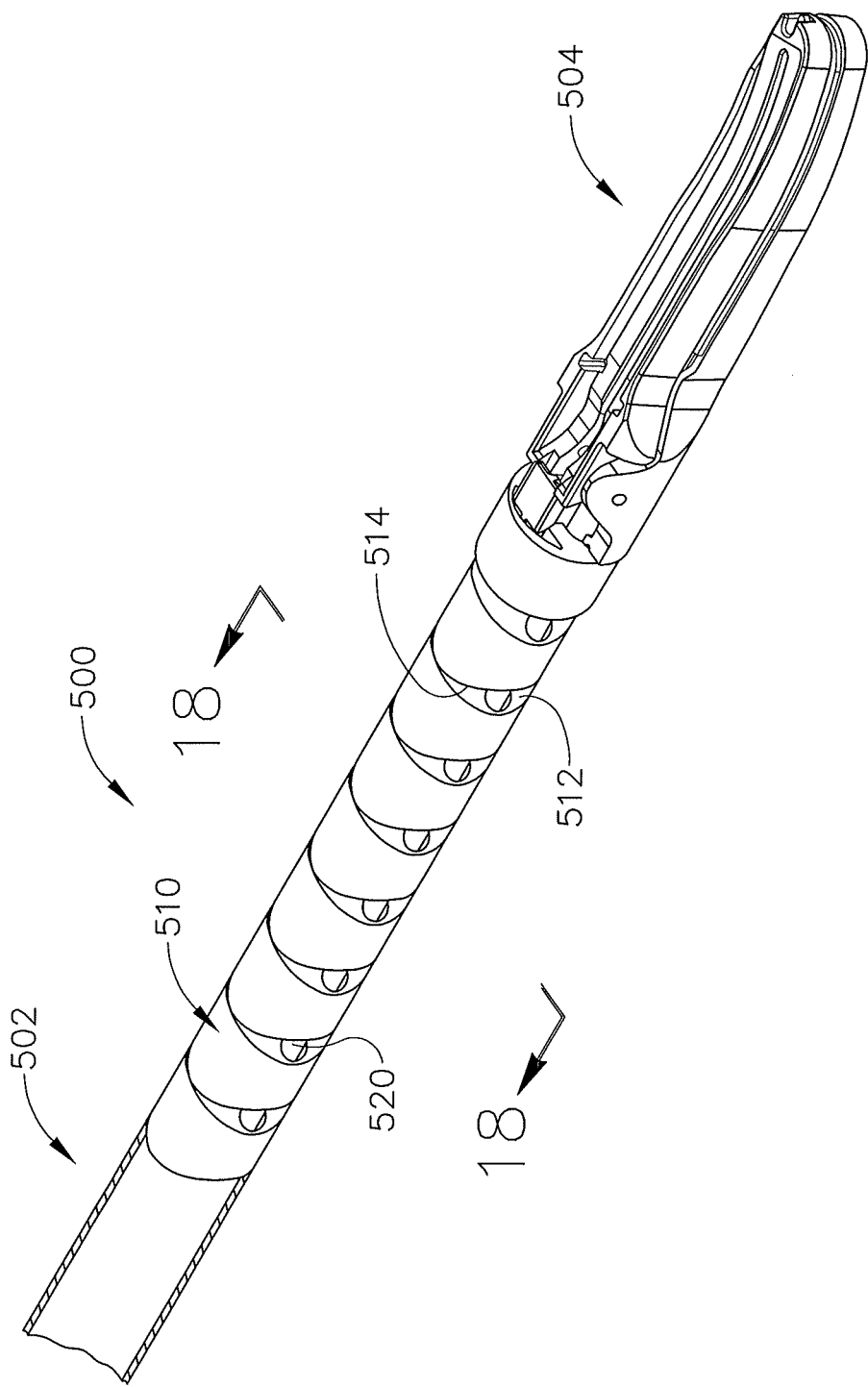
FIG. 16 depicts a perspective view of another exemplary articulation section for the shaft of the device of FIG. 1.
Figure 17:
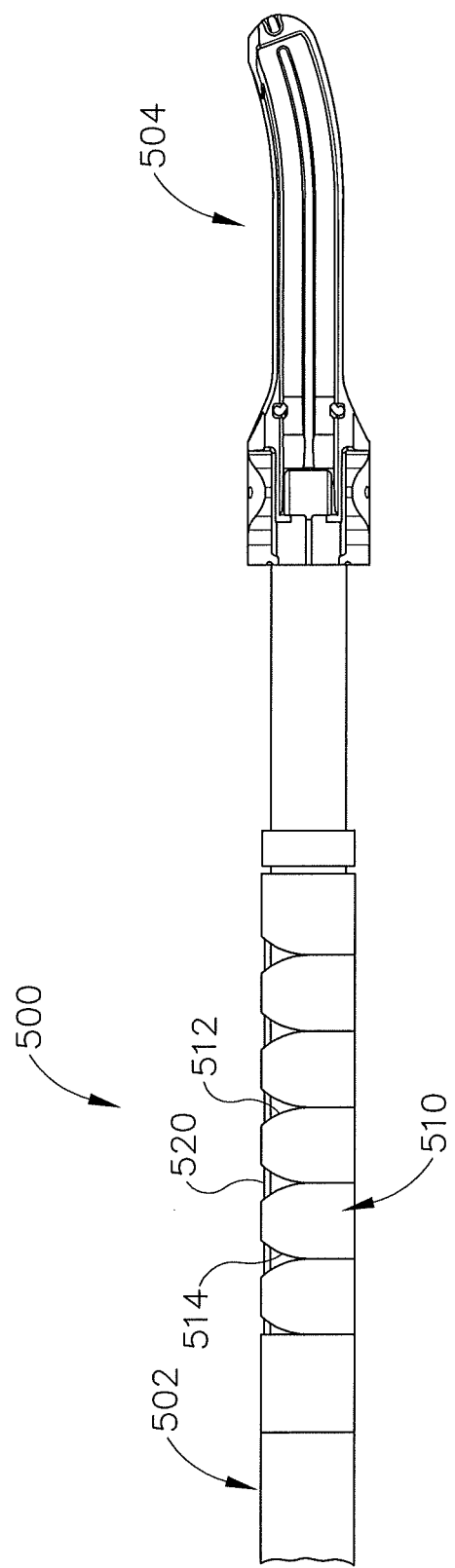
FIG. 17 depicts a bottom plan view of the articulation section of FIG. 16.
Figure 18:
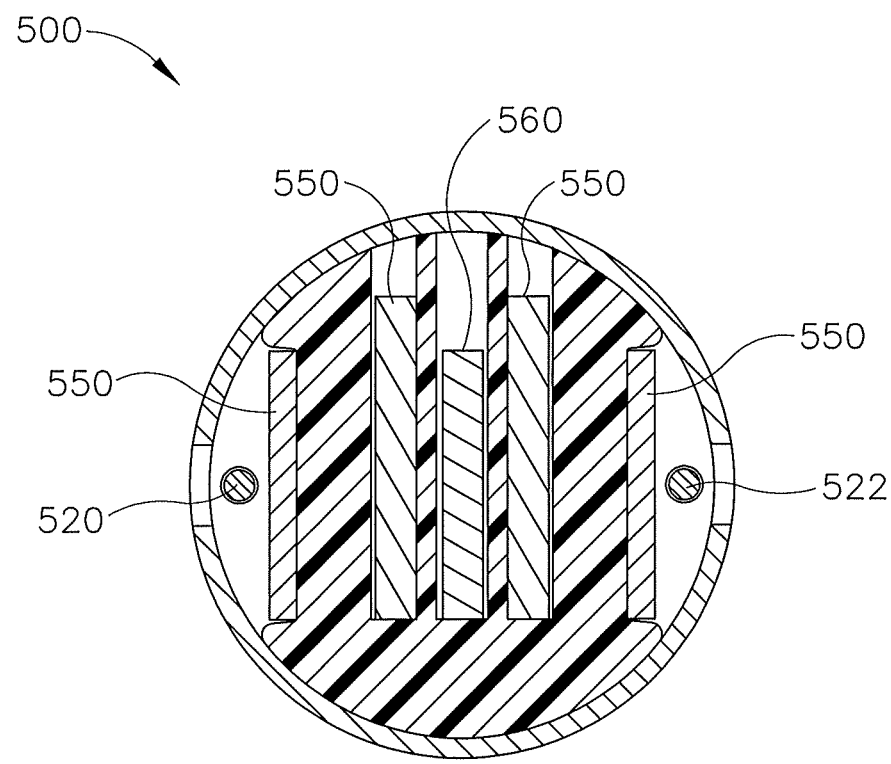
FIG. 18 depicts a cross-sectional view of a bead of the articulation section of FIG. 16, taken along line 18-18 of FIG. 16.

FIGS. 16-18 show another exemplary articulation section (500) disposed between a rigid shaft section (502) and an end effector (504). It should be understood that these features may be readily incorporated into electrosurgical instrument (10) described above, with shaft section (502) corresponding to shaft (30) and end effector (504) corresponding to end effector (40). Articulation section (500) of this example comprises a plurality of coaxially aligned beads (510). As best seen in FIG. 17, each bead (510) includes a first face (512) and a second face (514). One side of each first face (512) is convexly curved while the other side of first face (512) is substantially flat. Similarly, side of each second face (514) is convexly curved while the other side of second face (514) is substantially flat. Thus, the curved regions of faces (512, 514) define gaps when beads (510) are positioned in a line; while the flat regions of faces (512, 514) abut when beads (510) are positioned in a line. Such a configuration permits articulation section (500) to bend in one direction (i.e., on the side with the gaps) while preventing articulation section (500) from bending in the other direction (i.e., on the side lacking the gaps. It should be understood that the curved regions may instead be angled instead of being curved. It should also be understood that abutting curved regions of adjacent beads (510) may provide substantial lateral bending stiffness (e.g., when articulation section (500) is at or near a maximum degree of articulation).

As shown in FIG. 18, articulation section (500) also includes a plurality of support beams (550) that extend parallel to firing beam (560), which extends through the center of articulation section (500). As can also be seen in FIG. 18, an articulation cable (520) and an anchor cable (522) extend through articulation section (500). The longitudinal position of anchor cable (522) is fixed while articulation cable (520) is configured to translate. In particular, articulation cable (520) may be pulled proximally to articulate articulation section (500).

In some versions, support beams (550) are resiliently biased to orient articulation section (500) in a substantially straight configuration. This resilient bias may suffice to substantially straighten articulation section (500) when articulation cable (520) is released. This resilient bias may also reduce binding loads on firing beam (560) when firing beam (560) translates through articulation section (500) in a bent configuration. Beams (550) are also configured to enhance the structural integrity of articulation section (500), such as by providing resistance to lateral buckling or blowout of firing beam (560) when firing beam (560) translates through articulation section (500) in a bent configuration. Since beams (550) are separated from firing beam (560), beams (550) do not come into contact with firing beam (560) during operation of articulation section (500) and/or during operation of firing beam (560). This spacing may also reduce pinch loads of beams (550) on firing beam (560). In some other versions, support beams (550) are resiliently biased to orient articulation section (500) in a substantially bent configuration. In addition or in the alternative, firing beam (560) may be resiliently biased to assume a bent configuration through articulation section (500).

Figure 19:
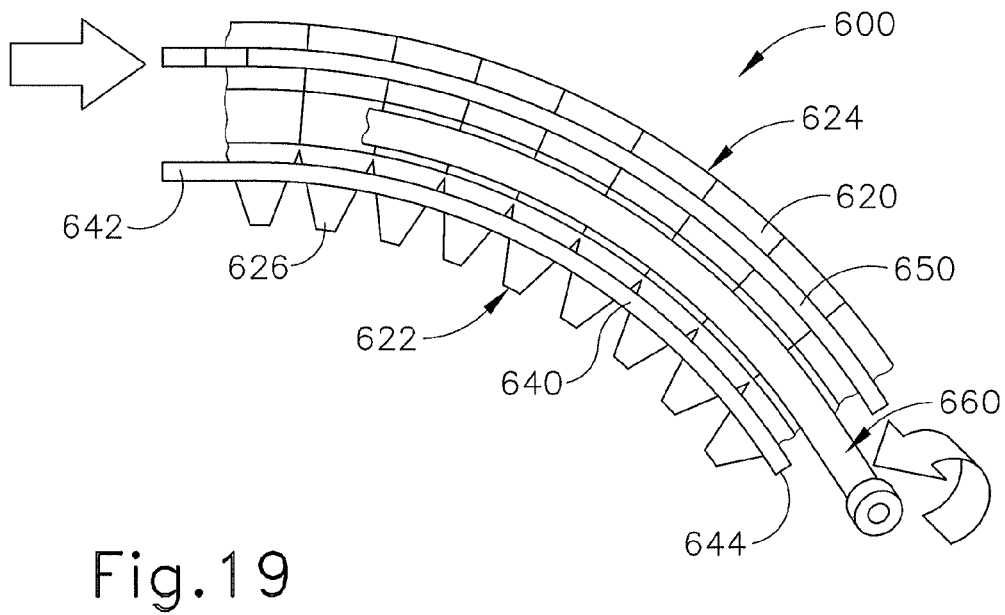
FIG. 19 depicts a partial cross-sectional top view of another exemplary articulation section for the shaft of the device of FIG. 1.
Figure 20:
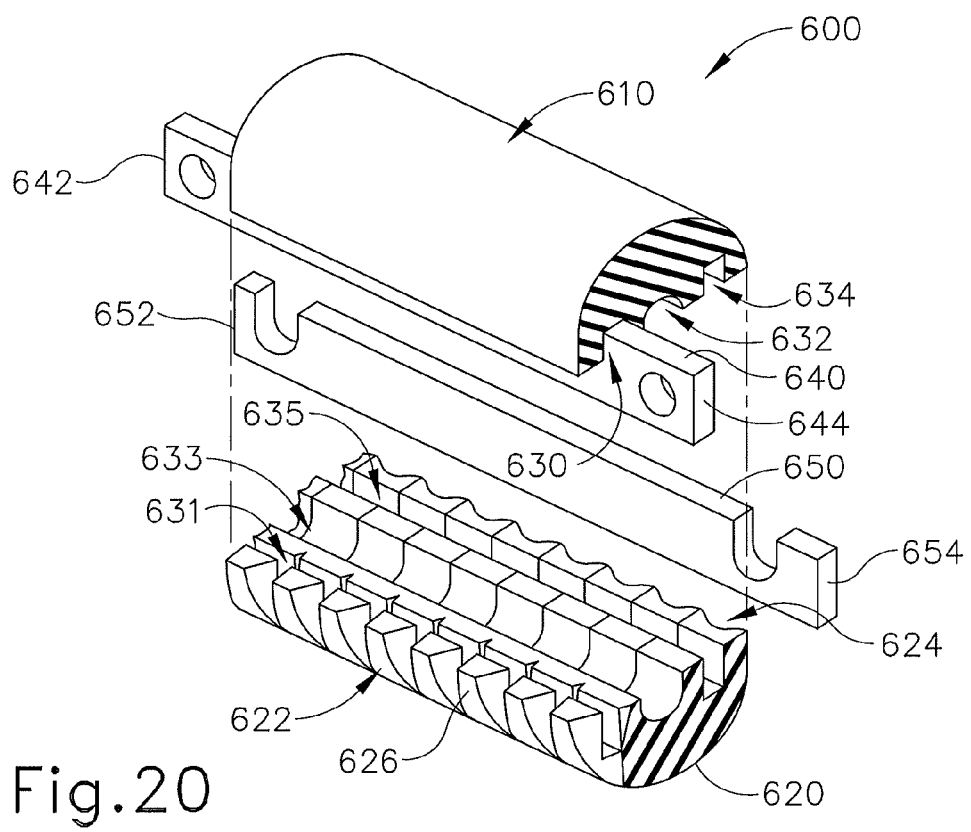
FIG. 20 depicts an exploded perspective view of the articulation section of FIG. 19.
Figure 21:
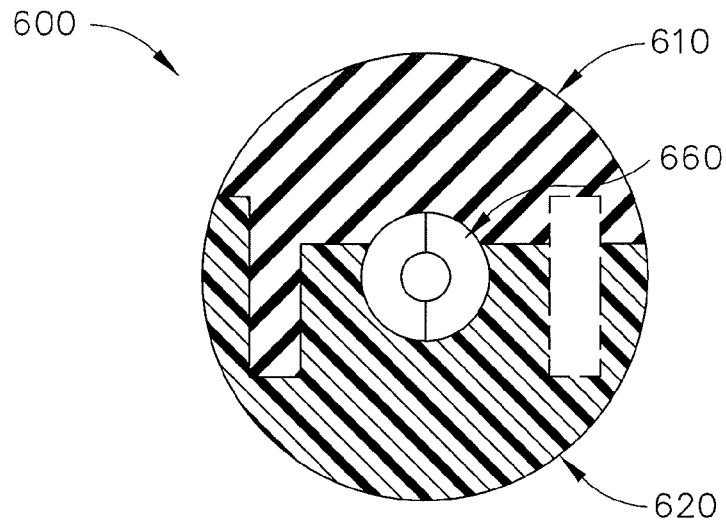
FIG. 21 depicts a cross-sectional end view of the articulation section of FIG. 19.

FIGS. 19-23 relate to yet another exemplary articulation section (600) that may be positioned between a rigid shaft section (such as any rigid shaft section referred to above) and an end effector (such as any end effector referred to above). It should be understood that these features may be readily incorporated into electrosurgical instrument (10) described above. Articulation section (600) of this example comprises an upper body (610) and a lower body (620). Bodies (610, 620) are configured to join together as best seen in FIG. 21. Body (610) of the present example is formed of a high durometer elastic material that is configured to resiliently assume a curved shape complementing the curvature shown in FIG. 19. Body (620) is formed of a flexible plastic such as nylon, polyethylene, isoplast, polypropylene, and/or various other materials. Body (620) may nevertheless be semi-rigid. In addition, body (620) is molded to assume the curved configuration shown in FIG. 19. As best seen in FIGS. 19-20, body (620) includes a stretched side (622) and a ribbed side (624). Ribbed side (624) comprises a plurality of spaced apart fins (626) that are configured to accommodate the bent configuration of body (620). It should be understood that stretched side (622) may also include fins (626) and/or various other features, if desired.

Body (610) also includes a plurality of recesses (630, 632, 634) running along the length of body (610). Body (620) also includes a plurality of recesses (631, 633, 634) running along the length of body (620). Recesses (630, 631) are configured to form a channel that receives a support band (640) when bodies (610, 620) are assembled together. Support band (640) extends along at least part of the length of articulation section (600). In some versions, one or both ends of support band (640) are secured relative to articulation section (600). In some other versions, both ends of support band (640) may move relative to articulation section (600). It should also be understood that support band (640) may be formed as a unitary feature of body (610), such that recess (630) is eliminated. In the present example, a proximal end (642) of support band (640) is secured to a rigid shaft section that is proximal to articulation section (600); while a distal end (644) of support band (640) is secured to an end effector that is distal to articulation section (600).

Recesses (632, 622) are configured to form a channel that receives an actuation rod (660), which will be described in greater detail below, when bodies (610, 620) are assembled together. It should be understood that actuation rod (660) may translate within articulation section (600) and rotate within articulation section (600). Recesses (634, 635) are configured to form a channel that receives an articulation band (650) when bodies (610, 620) are assembled together. It should be understood that at least a part of articulation band (650) may translate within articulation section (600). In the present example, a proximal end (652) of articulation band (650) is secured to a translating member of shaft section that is proximal to articulation section (600); while a distal end (654) of articulation band (650) is secured to an end effector that is distal to articulation section (600). When articulation band (650) is pulled proximally, articulation section (600) transitions from the curved/articulated configuration to a straight configuration depending on how far articulation band (650) is pulled. In some versions, articulation band (650) may be pulled further, such that articulation section (600) moves past a straight configuration and starts to bend/articulate in a direction opposite to its original bend/articulation.

Figure 22:
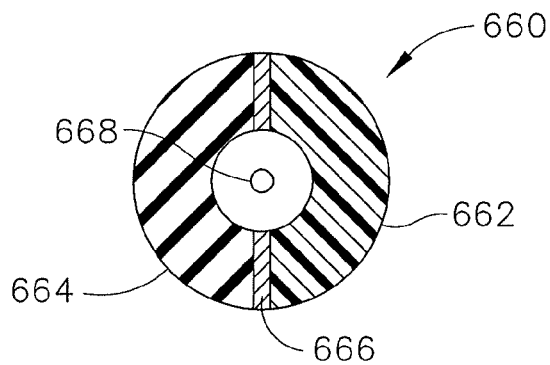
FIG. 22 depicts a cross-sectional end view of an end effector drive assembly for the articulation section of FIG. 19.

FIG. 22 shows actuation rod (660) in greater detail. Actuation rod (660) is operable to translate a firing beam, knife, and/or other feature of an end effector that is distal to articulation section (600). In addition or in the alternative, actuation rod (660) may be operable to rotate at least a part of such an end effector, if not the entire end effector, relative to articulation section (600). In the present example, actuation rod (660) comprises a translating section (662), a mechanical ground section (664), and an insulating section (666). Translating section (662) and mechanical section (664) have opposing "C" shapes, with insulating section (666) being interposed between translating section (662) and mechanical section (664). Translating section (662) is operable to translate within articulation section (600), to translate a firing beam, knife, and/or other feature of an end effector that is distal to articulation section (600); while mechanical ground section (664) remains stationary, providing a mechanical ground that acts as a spine to structurally support the end effector that is distal to articulation section (600). Insulating section (666) provides electrical isolation between sections (662, 664). In addition, a wire (668) extends through the center of actuation rod (660) to provide electrical communication between the end effector and a power source. Wire (668) may also be insulated relative to sections (662, 664)

Figure 23:
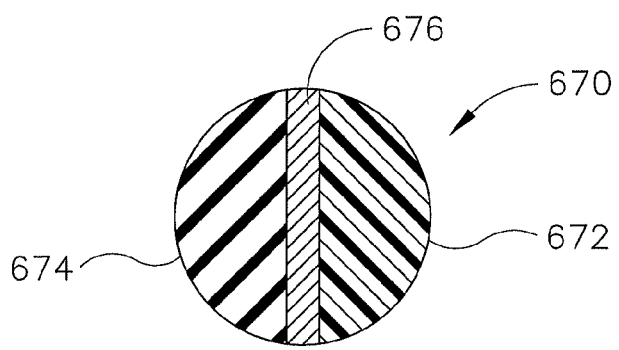
FIG. 23 depicts a cross-sectional end view of another exemplary end effector drive assembly for the articulation section of FIG. 19.

FIG. 23 shows a merely illustrative variation of actuation rod (660). Actuation rod (670) of this example comprises a translating section (672), a mechanical ground section (674), and an insulating section (676). In this example, sections (672, 674) have opposing flat faces instead of having the "C" shaped configuration of sections (662, 664). In addition, insulating section (676) of this example comprises a flat plate. Actuation rod (670) lacks a wire (668). For instance, a wire may instead run through a different part of articulation section (600). Actuation rod (670) is otherwise essentially the same as actuation rod (660). Other suitable components, features, and configurations for an actuation rod (660) will be apparent to those of ordinary skill in the art in view of the teachings herein.

F. Exemplary Hinged Articulation Section

Figure 24:
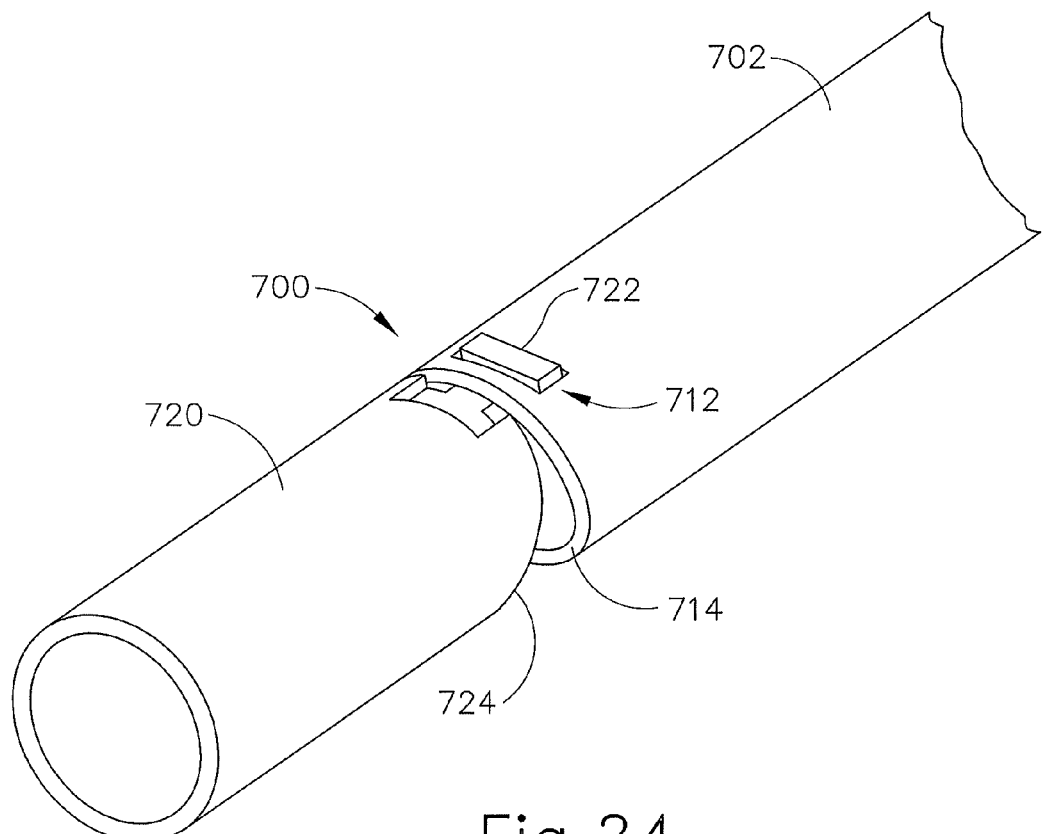
FIG. 24 depicts a perspective view of another exemplary articulation section for the shaft of the device of FIG. 1.
Figure 25:
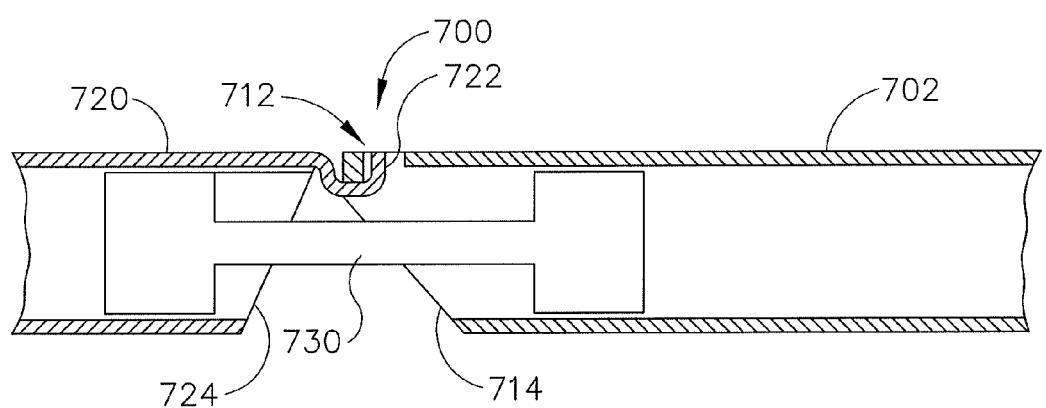
FIG. 25 depicts a cross-sectional side view of the articulation section of FIG. 24.

FIGS. 24-25 show an exemplary articulation section (700) that may be used to join a rigid shaft section (702) and an end effector. It should be understood that these features may be readily incorporated into electrosurgical instrument (10) described above, with shaft section (702) corresponding to shaft (30) and the end effector corresponding to end effector (40). Articulation section (700) of this example comprises a distal hinge cuff (720) that is hingedly coupled with shaft section (702). In particular, cuff (720) includes a proximally projecting prong (722) that is received in a transverse opening (712) formed at the distal end of shaft section (702). Prong (722) thus forms a pivoting hinge coupling cuff (720) with shaft section (702). Cuff (720) is secured to a proximal portion of an end effector (not shown), such that the end effector will pivot with cuff (720) relative to shaft section (702).

A flex member (730) spans from shaft section (702) to cuff (720). Flex member (730) may house a firing beam to actuate a portion of the end effector. Flex member (730) may also house one or more articulation bands, cables, or other features that are operable to articulate cuff (720). Various suitable forms that flex member (730) and associated components may take will be apparent to those of ordinary skill in the art in view of the teachings herein.

As best seen in FIG. 25, the distal end of shaft section (702) includes an angled edge (724). In addition, the proximal end of cuff (720) includes an angled edge (724). The angles and orientations of edges (714, 724) are configured to accommodate pivoting of cuff (720) both away from and over the longitudinal axis of shaft section (702). In some other versions, only one edge (714, 724) is angled while the other edge (714, 724) is substantially perpendicular to the longitudinal axis of shaft section (702). As another merely illustrative variation both edges (714, 724) may be substantially perpendicular to the longitudinal axis of shaft section (702). In some such versions, cuff (720) can only pivot away from the longitudinal axis of shaft section (702) without being able to also pivot over and past the longitudinal axis of shaft section (702). Still other suitable components, features, configurations, and operabilities for pivoting section (700) will be apparent to those of ordinary skill in the art in view of the teachings herein.

G. Exemplary Articulation Section with Helical Configuration

Figure 26:
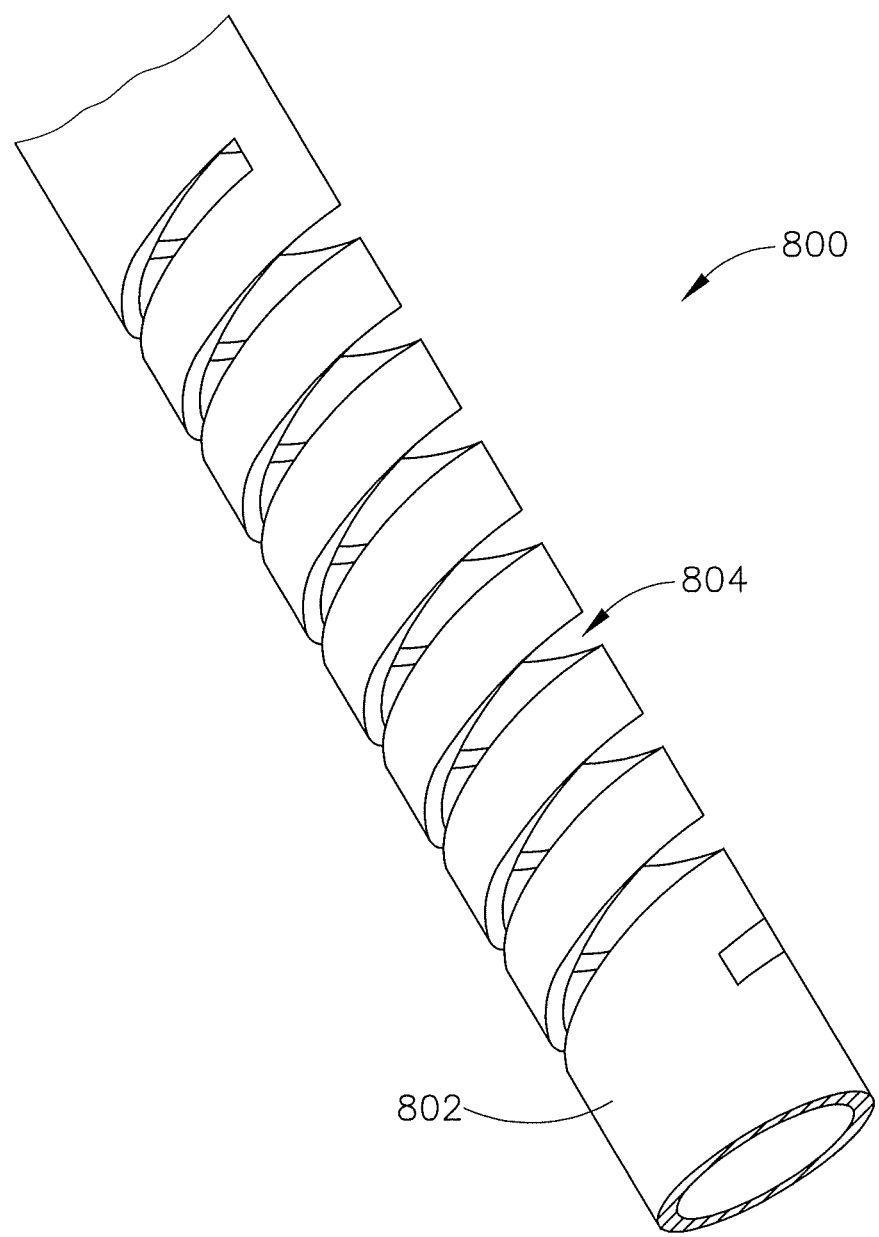
FIG. 26 depicts a perspective view of another exemplary articulation section for the shaft of the device of FIG. 1.

FIG. 26 shows another exemplary articulation section (800) that may be positioned between a rigid shaft section (such as any rigid shaft section referred to above) and an end effector (such as any end effector referred to above). It should be understood that these features may be readily incorporated into electrosurgical instrument (10) described above. Articulation section (800) of this example comprises a tube member (802) having a helical cutout (804) formed therein. Helical cutout (804) may facilitate bending of tube member (802), thereby facilitating articulation of an end effector that is positioned distal to tube member (802). Various components such as a firing bar, articulation bands/cables/etc., a wire, etc. may pass through tube member (802). It should also be understood that a flexible shrink wrap or other component may be positioned about helical cutout (804) (e.g., to prevent tissue from being pinched during articulation). Tube member (802) may be formed of any suitable flexible material, and may be resiliently biased to assume a substantially straight configuration. Helical cutout (804) may be formed using any suitable techniques, including but not limited to molding or machining (e.g., laser cut, wire EDM, milling, etc.). It should also be understood that tube member (802) may simply be a unitary distal portion of a rigid shaft member that extends all the way to the handpiece or other type of body portion of the instrument.

Figure 27:
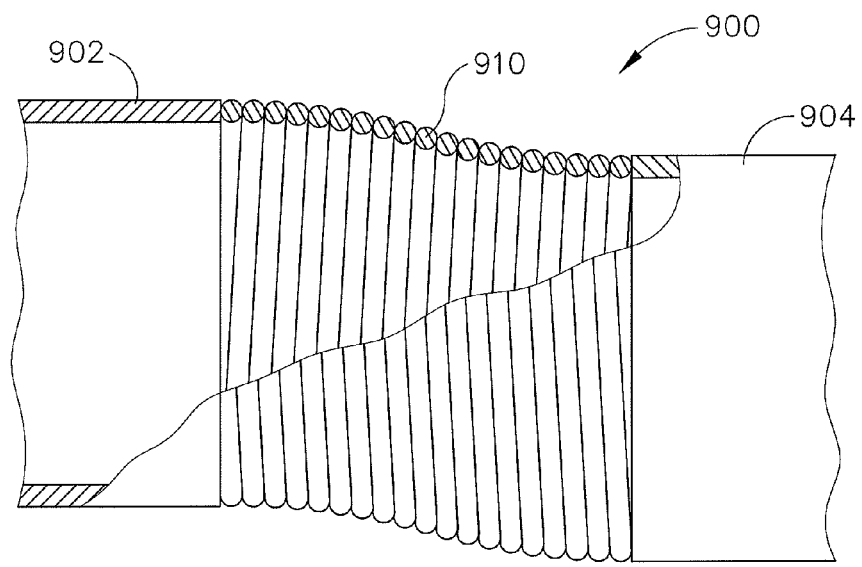
FIG. 27 depicts a partial cross-sectional side view of another exemplary articulation section for the shaft of the device of FIG. 1.

FIG. 27 shows another helically configured articulation section (900), which is disposed between a rigid shaft section (902) and an end effector (904). It should be understood that these features may be readily incorporated into electrosurgical instrument (10) described above, with shaft section (902) corresponding to shaft (30) and end effector (904) corresponding to end effector (40). Articulation section (900) of this example comprises a coil spring (910). By way of example only, coil spring (910) may comprise a conventionally formed metal coil spring that is welded to rigid shaft section (902) and end effector (904). Of course, any other suitable materials may be used, and any other suitable techniques for coupling coil spring (910) may be used. Coil spring (910) may be selectively bent relative to a longitudinal axis defined by rigid shaft section (902), thereby facilitating articulation of end effector (904). Coil spring (910) may be resiliently biased to assume a substantially straight configuration. Various components such as a firing bar, articulation bands/cables/etc., a wire, etc. may pass through coil spring (910). It should also be understood that a flexible shrink wrap or other component may be positioned about coil spring (910) (e.g., to prevent tissue from being pinched during articulation). Other suitable forms for a helically configured articulation section will be apparent to those of ordinary skill in the art in view of the teachings herein.

H. Exemplary Articulation Section with Single Pivot

Figure 28:
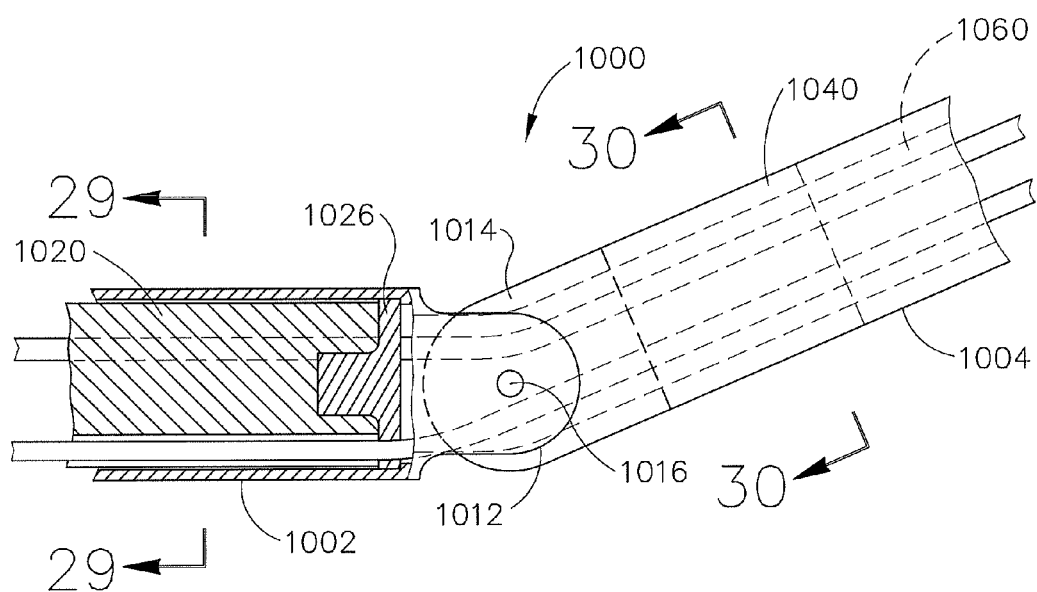
FIG. 28 depicts a schematic view of another exemplary articulation section for the shaft of the device of FIG. 1.

FIG. 28 shows an articulation joint (1000) that is used to pivotally couple a rigid shaft section (1002) with an end effector (1004). It should be understood that these features may be readily incorporated into electrosurgical instrument (10) described above, with shaft section (1002) corresponding to shaft (30) and end effector (1004) corresponding to end effector (40). Articulation joint (1000) of this example is formed by a pair of clevis features (1012, 1014) that are joined by a pair of pins (1016). In particular, the distal end of rigid shaft section (1002) includes a clevis feature (1012) while the proximal end of end effector (1014) also includes a clevis feature (1014). Clevis feature (1014) fits within clevis feature (1012), such that clevis feature (1012) overlaps and encompasses clevis feature (1014). Of course, any other suitable relationships may be used. Clevis features (1012, 1014) each include a respective upper tongue and lower tongue. An upper pin (1016) pivotally couples the upper tongues of clevis features (1012, 1014) together, while a lower pin (not shown) pivotally couples the lower tongues of clevis features (1012, 1014) together. Thus, clevis features (1012, 1014) and pins (1016) enable pivoting of end effector (1004) relative to shaft section (1002). Having pins (1016) separated (e.g., instead of having a single pin passing through the entire diameters of rigid shaft section (1002) and end effector (1004), etc.) facilitates passage of components through articulation joint (1000) as described below.

Figure 29:
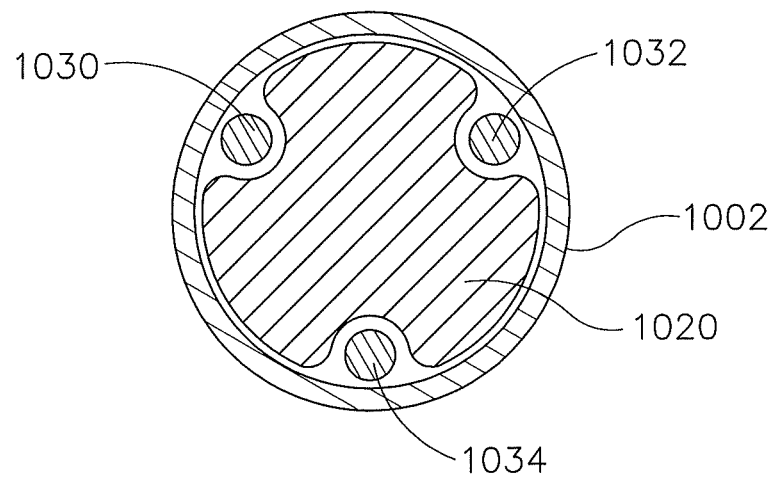
FIG. 29 depicts a cross-sectional view of a shaft portion of the articulation section of FIG. 28, taken along line 29-29 of FIG. 28.

Rigid shaft section (1002) of the present example includes a pusher (1020), as best seen in FIG. 29. Pusher (1020) is configured to translate longitudinally within rigid shaft section (1002). Pusher (1020) includes longitudinally extending recesses that are configured to receive a pair of articulation cables (1030, 1032) and a wire (1034). Pusher (1020) is configured to keep cables (1030, 1032) and wire (1034) spaced apart from each other while enabling cables (1030, 1032) and wire (1034) to translate within shaft section (1002), independent of each other. Articulation cables (1030, 1032) are operable to selectively articulate end effector (1004) in accordance with the teachings herein. Wire (1034) is operable to communicate electrical power from a power source to end effector (1004) in accordance with the teachings herein. Pusher (1020) of the present example also keeps cables (1030, 1034) electrically isolated from wire (1034). Pusher (1020) of the present example is formed of a plastic extrusion, though it should be understood that any other suitable materials and/or processes may be used.

Pusher (1020) is coupled with a firing beam (1060), which extends through end effector (1004) and which is configured and operable in accordance with firing beam (60) described above. Firing beam (1060) is secured to pusher (1020) via a threaded coupling (1026), as shown in FIG. 28, though it should be understood that any other suitable type of coupling may be used. It should also be understood that pusher (1020) may be reciprocated within rigid shaft section (1002) in order to reciprocate firing beam (1060) within end effector (1004).

Figure 30:
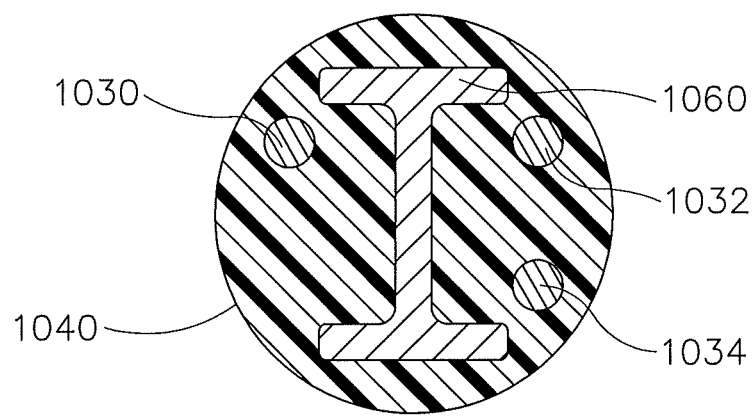
FIG. 30 depicts a cross-sectional view of an end effector portion of the articulation section of FIG. 28, taken along line 30-30 of FIG. 28.

End effector (1004) of the present example further includes an insert (1040), as best seen in FIG. 30. Insert (1040) includes passages to receive firing beam (1060), cables (1030, 1032), and wire (1034). Insert (1040) is fixed within end effector (1004) in this example. However, insert is configured to enable translation of firing beam (1060) through insert (1040). In some versions, one or both of cables (1030, 1032) are also translatable through insert (1040), though it should be understood that one or both of cables (1030, 1032) may be fixedly secured to insert (1040). Similarly, wire (1034) may be fixedly secured relative to insert (1040) or may translate relative to insert (1040). In each of these scenarios, insert (1040) is configured to keep firing beam (1060), cables (1030, 1032), and wire (1034) spaced apart from each other. Insert (1040) of the present example also keeps cables (1030, 1034), firing beam (1060), and wire (1034) electrically isolated from each other. Insert (1040) of the present example is formed of a plastic extrusion, though it should be understood that any other suitable materials and/or processes may be used.

Wire (1034) of the present example is formed as a resilient coil. This coiled configuration enables wire (1034) to extend in effective length when end effector (1004) is articulated relative to rigid shaft section (1002), with wire (1034) retracting back to a shorter effective length when end effector (1004) is moved back to a position that is substantially aligned with rigid shaft section (1002).

I. Exemplary Articulation Section with Angled Joint

Figure 31A:
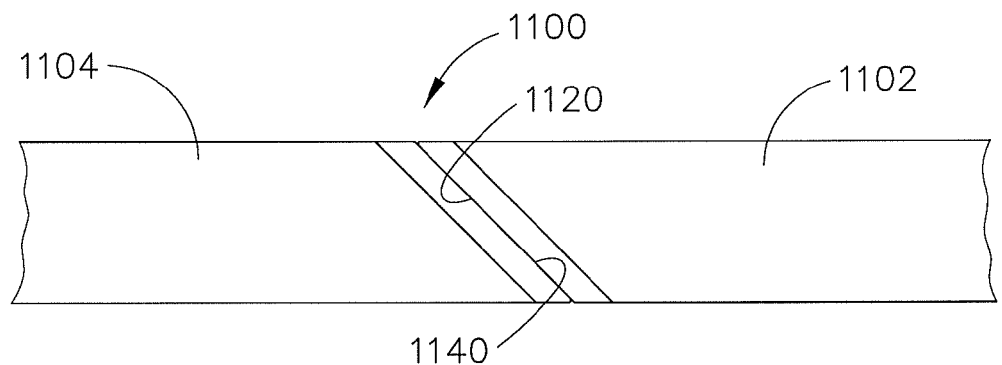
FIG. 31A depicts a side elevational view of another exemplary articulation section for the shaft of the device of FIG. 1, in a substantially straight configuration.
Figure 31B:
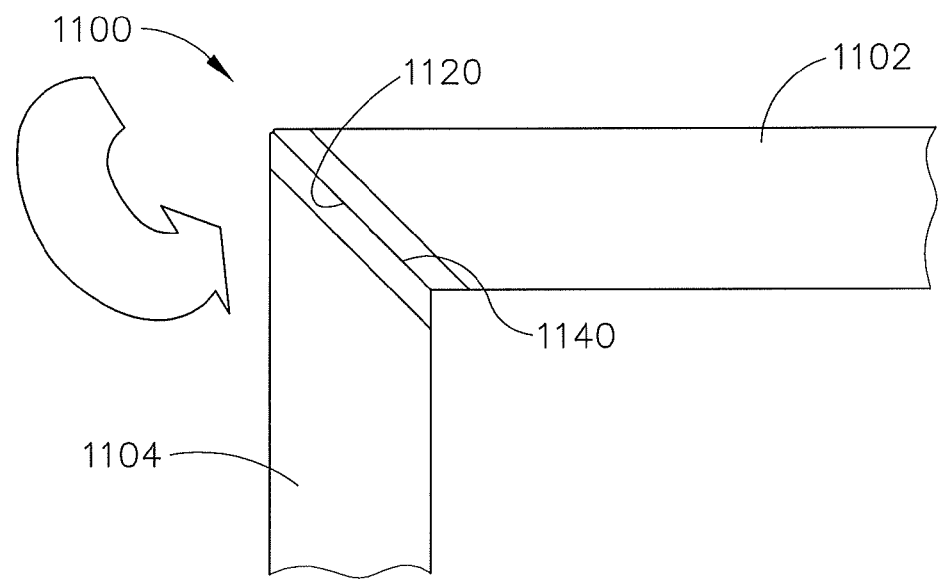
FIG. 31B depicts a side elevational view of the articulation section of FIG. 31A, in an articulated configuration.

FIGS. 31A-31B show an articulation joint (1100) that is used to pivotally couple a rigid shaft section (1102) with an end effector (1104). It should be understood that these features may be readily incorporated into electrosurgical instrument (10) described above, with shaft section (1102) corresponding to shaft (30) and end effector (1104) corresponding to end effector (40). Articulation joint (1100) of this example is formed by complementary angled edges (1120, 1140) formed at the distal end of rigid shaft section (1102) and the proximal end of end effector (1104), respectively. As can be seen from the transition from FIG. 31A to FIG. 31B, the camming relationship of these edges (1120, 1140) provides articulation of end effector (1104) upon rotation of end effector (1104) relative to rigid shaft section (1102). Various suitable ways in which end effector (1104) may be rotated relative to rigid shaft section (1102) will be apparent to those of ordinary skill in the art in view of the teachings herein. Similarly, various suitable ways in which components may pass through articulation joint (1100) and still function properly when end effector (1104) is rotated and articulated relative to rigid shaft section (1102) will be apparent to those of ordinary skill in the art in view of the teachings herein. While edges (1120, 1140) at an angle of approximately 45° in the present example, it should be understood that any other suitable angle may be used.

In some versions, a firing beam (not shown, but analogous to firing beam (60)) is used to stabilize the distal end of end effector (1104) when the articulation angle of end effector (1104) is adjusted. For instance, rigid shaft section (1102) and end effector (1104) may be configured to selectively separate from each other to facilitate articulation. With edges (1120, 1140) being separated from each other, but with the firing beam still keeping end effector (1104) coupled with a handpiece or other type of instrument body, rigid shaft section (1102) may be rotated to change the position of edge (1120). Once edge (1120) has reached a position corresponding to a desired articulation angle, end effector (1104) may be pulled proximally toward rigid shaft section (1102) until edges (1120, 1140) engage. This engagement will cause end effector (1104) to deflect in an articulated manner. Then, the user may secure the longitudinal position of end effector (1104) relative to rigid shaft section (1102) to maintain the desired articulation angle. It should also be understood that edges (1120, 1140) may include complementary electrical contacts, which may be used to communicate power from a power source to end effector (1104). Other suitable variations of angled joint (1100) will be apparent to those of ordinary skill in the art in view of the teachings herein.

J. Exemplary Articulation Section with Preformed Bend

Figure 32:
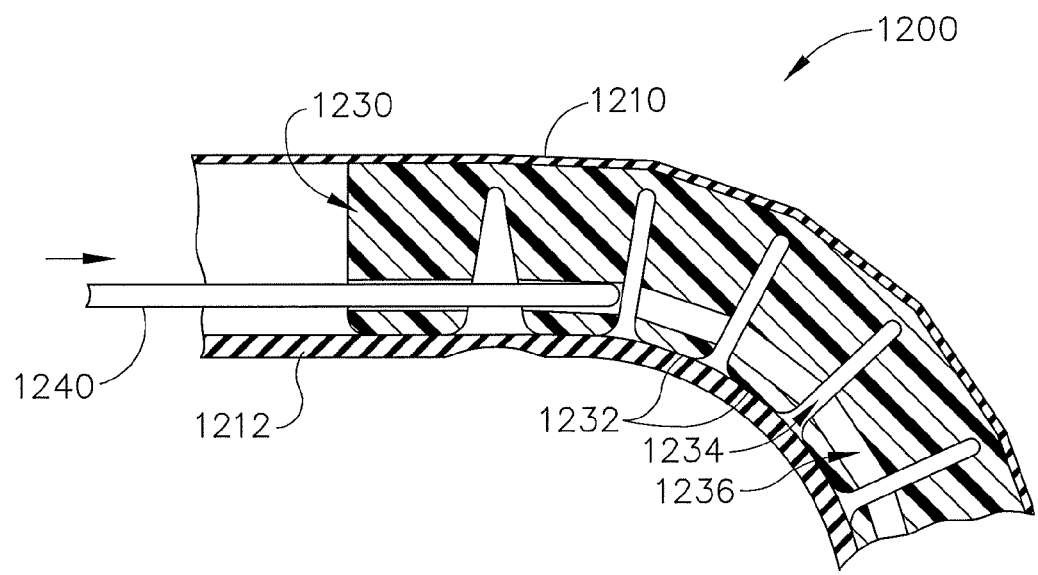
FIG. 32 depicts a cross-sectional view of another exemplary articulation section for the shaft of the device of FIG. 1, in an articulated configuration.
Figure 33:
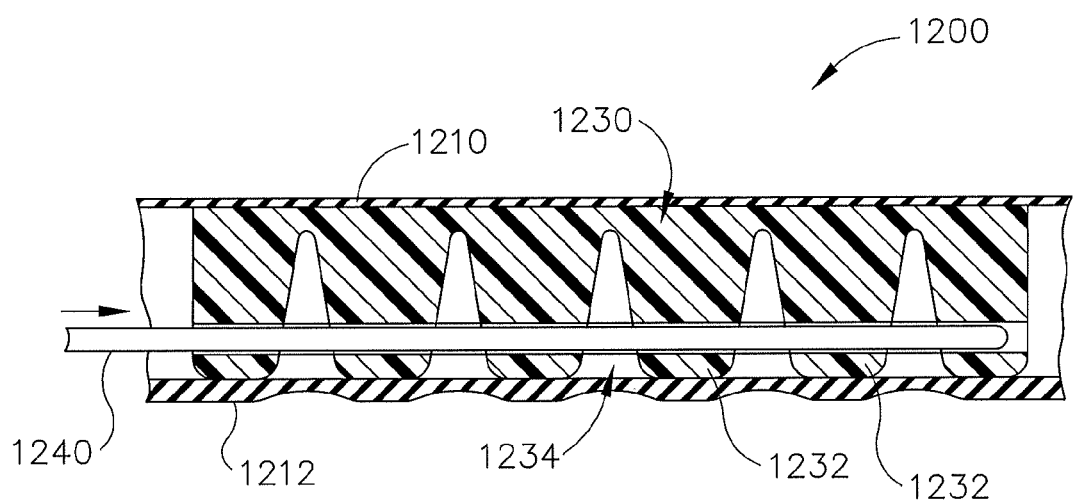
FIG. 33 depicts a cross-sectional view of the articulation section of FIG. 32, in a substantially straight configuration.

FIGS. 32-33 show another exemplary articulation section (1200) that may be positioned between a rigid shaft section (such as any rigid shaft section referred to above) and an end effector (such as any end effector referred to above). It should be understood that these features may be readily incorporated into electrosurgical instrument (10) described above. Articulation section (1200) of this example comprises a sheath (1210), an insert (1230), and a reciprocating rod (1240).

Sheath (1210) is formed of a flexible material that readily transitions between the bent configuration shown in FIG. 32 and the substantially straight configuration shown in FIG. 33. Insert (1230) is formed of a resilient and semi-rigid material that is biased to assume the curved configuration shown in FIG. 32. For instance, insert (1230) may be molded or otherwise preformed to form the curved configuration shown in FIG. 32. Insert (1230) includes a plurality of rib members (1232) that are spaced apart by recesses (1234). The angles of the sidewalls of rib members (1232) are selected to restrict the maximum articulation angle of articulation section (1200). In particular, the articulation angle may be at a maximum when the sidewalls or each rib member (1232) is in full contact with the sidewall of the adjacent rib member (1232).

Each rib member (1232) includes a passageway (1236) that is configured to slidingly receive rod (1240). Passageways (1236) are positioned along an inner radius of the bend formed by insert (1230) in this example, though it should be understood that passageways (1236) may be otherwise positioned. Rod (1240) is a substantially rigid member that is configured to substantially straighten insert (1230) as rod (1240) is inserted through rib members (1232). Thus, the end effector is articulated relative to the rigid shaft section when rod (1240) is in a proximal position as shown in FIG. 32; while the end effector is substantially aligned with the rigid shaft section when rod (1240) is in a distal position as shown in FIG. 33. The end effector may be selectively positioned at any suitable degree of articulation based on the longitudinal positioning of rod (1240) (e.g., rod (1240) being positioned anywhere between a proximal-most position and a distal-most position, etc.). By way of example only, articulation section (1200) may be configured to enable the end effector to sweep through a range of articulation angles between approximately 0° and approximately 130° relative to the rigid shaft section. As another merely illustrative example, the maximum articulation angle may be up to approximately 160°. Other suitable angles and ranges will be apparent to those of ordinary skill in the art in view of the teachings herein.

The longitudinal position of rod (1240) may be selectively secured to selectively secure the articulation angle of the end effector. Various suitable features for translating and securing rod (1240) will be apparent to those of ordinary skill in the art in view of the teachings herein. It should also be understood that passageways (1236) may each have a tapered configuration (e.g., proximal side wider than distal side) to facilitate insertion of rod (1240) in passageways (1236) as rod (1240) is advanced distally. Insert (1230) may also include passageways to accommodate other features such as one or more wires, a firing beam, etc. In addition, sheath (1210) may include an integral elastomeric band (1212) and/or other feature at the inner radius of the curve formed by insert (1230) to help stabilize the articulation angle of articulation section (1200).

Figure 34:
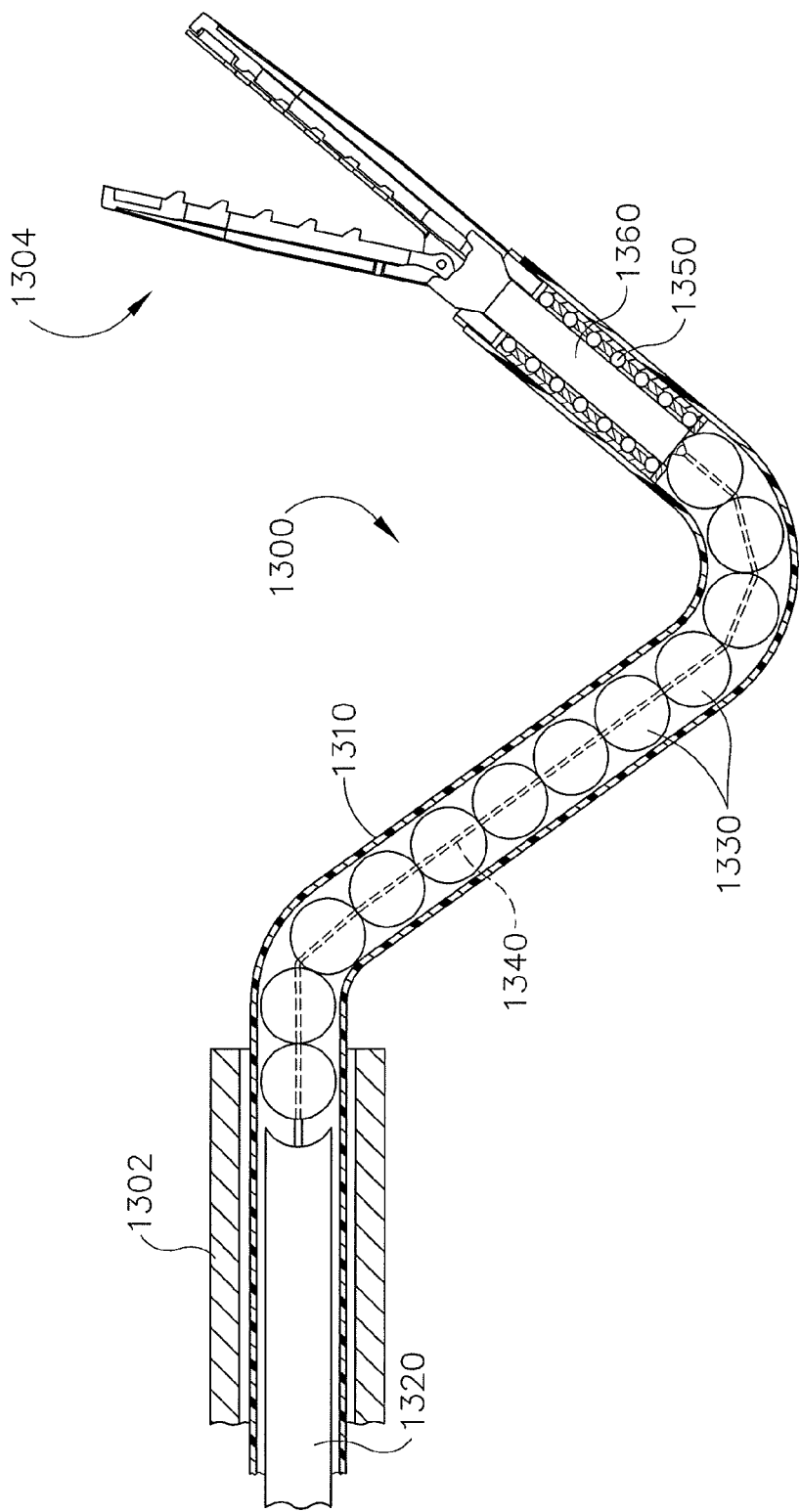
FIG. 34 depicts a cross-sectional view of another exemplary articulation section for the shaft of the device of FIG. 1.

FIG. 34 shows exemplary components and configurations that may be used to actuate a firing beam through a pre-bent articulation section (1300). In this example, articulation section (1300) includes sheath (1310) that is preformed to include a pair of bends that position an end effector (1304) at an angle relative to a rigid shaft section (1302). It should be understood that these features may be readily incorporated into electrosurgical instrument (10) described above, with shaft section (1302) corresponding to shaft (30) and end effector (1304) corresponding to end effector (40). In some versions (1310), sheath (1310) is resiliently biased to assume the configuration shown in FIG. 34, but may be selectively straightened in order to pass through a trocar or other cannula in order to reach the interior of a patient in a minimally invasive manner.

In the example shown in FIG. 34, a push rod (1320) is slidably positioned within a proximal portion of sheath (1310). A plurality of bearings (1330) are positioned adjacent to one another within sheath (1310), distal to push rod (1320). A wire (1340) passes through bearings (1330), such that bearings (1330) are tethered together by wire (1340). Wire (1340) is configured to communicate power from a power source to end effector (1304). Bearings (1330) are configured to translate within sheath (1310) and are thus operable to transmit distal translational motion from push rod (1320) to firing beam (1360). Firing beam (1360) is thereby operable in accordance with firing beam (60) as described above. In the present example, bearings (1330) translate along the bent path formed by sheath (1310) without straightening sheath when bearings (1330) are advanced distally. Wire (1340) is structurally coupled to firing beam (1360) and push rod (1320) such that wire (1340) is operable to retract firing beam (1360) proximally when push rod (1320) is retracted proximally. Thus, end effector (1340) may be opened by retracting push rod. A set of bearings (1350) are used support firing beam (1360) in this example, though it should be understood that various alternative structures may be used.

K. Exemplary Articulation Section with Offset Hinge

Figure 35:
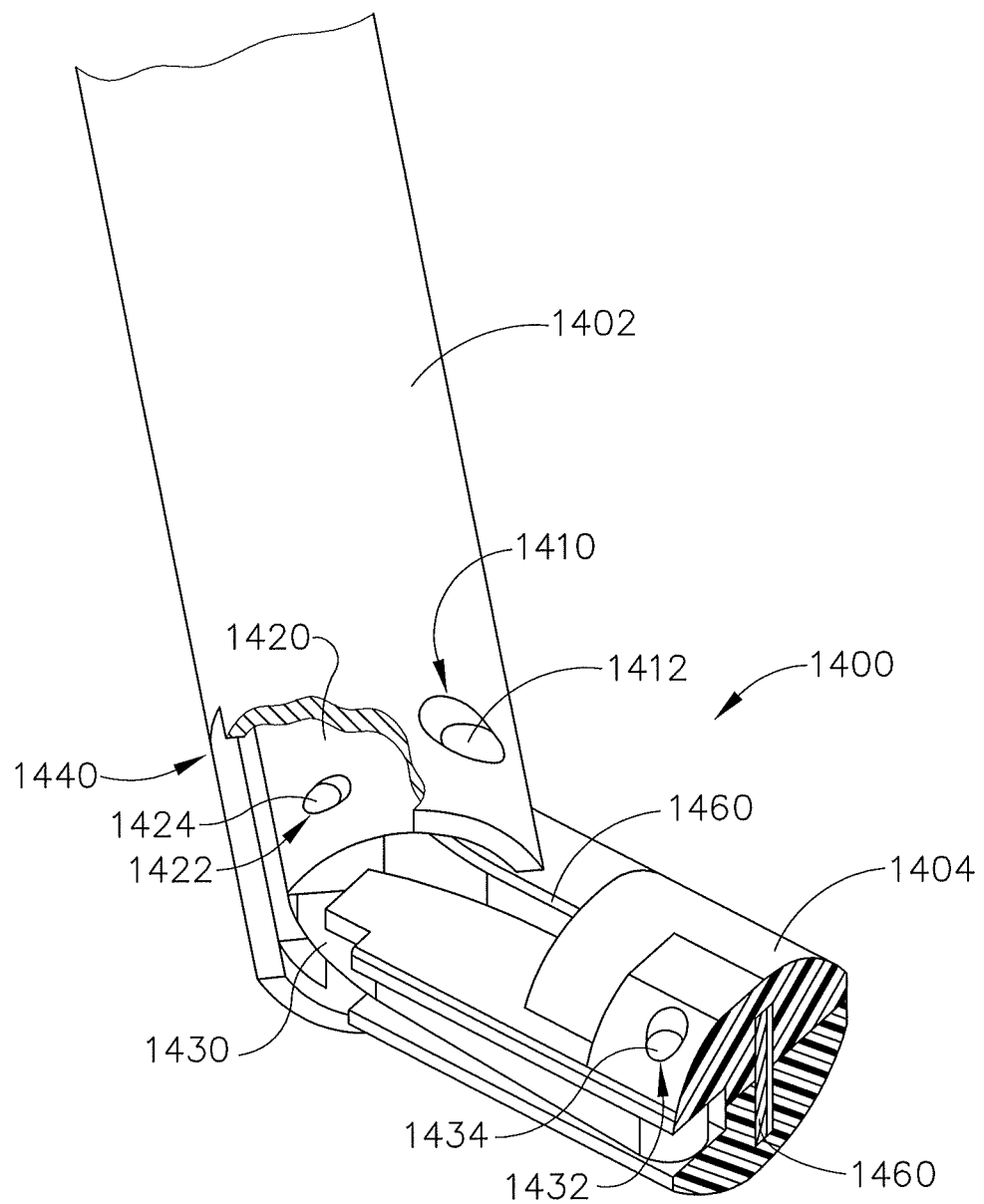
FIG. 35 depicts a perspective view of another exemplary articulation section for the shaft of the device of FIG. 1.
Figure 36:
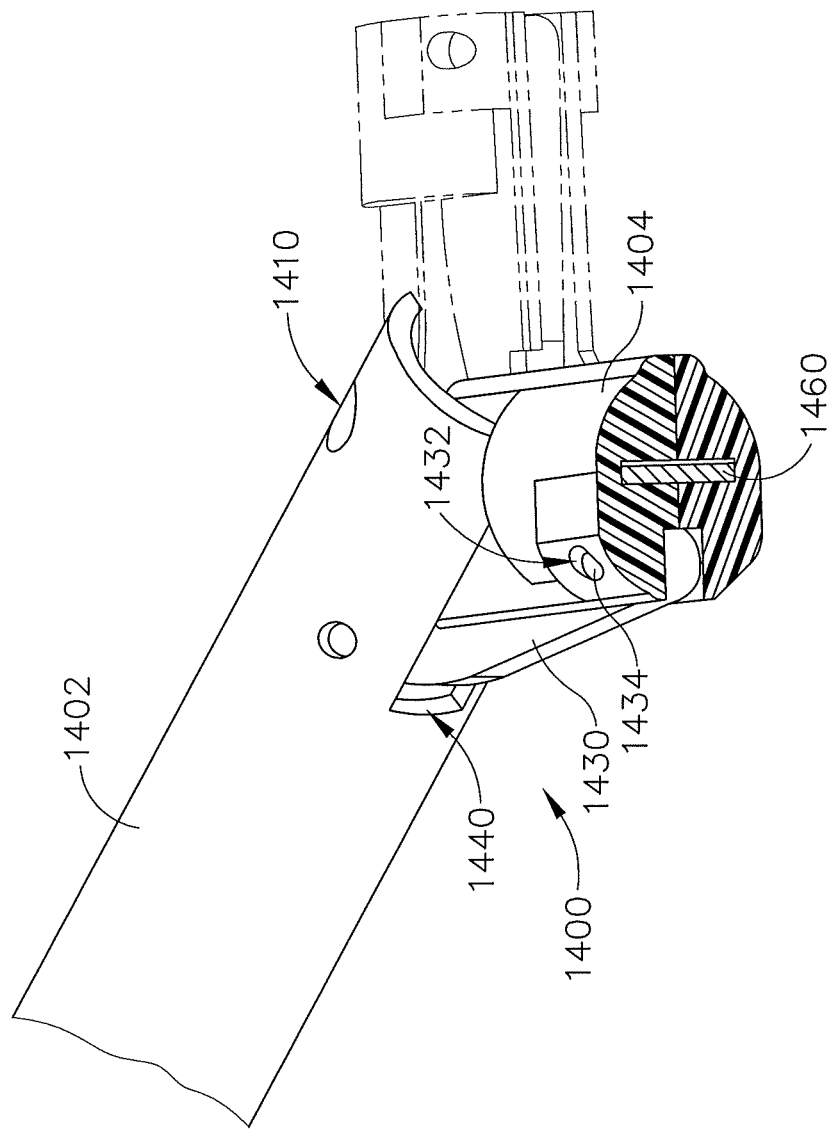
FIG. 36 depicts another perspective view of the articulation section of FIG. 35.

FIGS. 35-36 show an articulation joint (1400) that is used to pivotally couple a rigid shaft section (1402) with an end effector (1404). It should be understood that these features may be readily incorporated into electrosurgical instrument (10) described above, with shaft section (1402) corresponding to shaft (30) and end effector (1404) corresponding to end effector (40). Articulation joint (1400) of this example comprises a pivot (1410) that is provided at the distal end of rigid shaft section (1402), laterally offset from the longitudinal axis of rigid shaft section (1402). End effector (1404) is pivotally coupled with rigid shaft section (1402) at pivot (1410) by a pin (1412).

A rigid, elongate articulation member (1420) is slidably disposed within shaft section (1402). Articulation member (1420) is laterally offset from the longitudinal axis of rigid shaft section (1402), substantially opposite to the offset position of pivot (1410). The distal end of articulation member (1420) includes a pivot (1422). A linkage (1430) is pivotally coupled with articulation member (1420) at pivot (1422) by a pin (1424). Articulation member (1420) and linkage (1430) are configured such that linkage (1430) will move in response to proximal and distal translation of articulation member (1420). Various suitable features that may be provided for translation of articulation member (1420) will be apparent to those of ordinary skill in the art in view of the teachings herein.

The distal end of linkage (1430) also includes a pivot (1432). In particular, linkage (1430) is pivotally coupled with end effector (1404) at pivot (1432) by a pin (1434). Linkage (1430) and end effector (1404) are configured such that end effector will pivot about pivot (1410) in response to movement of linkage (1430). Since linkage (1430) is also coupled with articulation member (1420), it will be understood that end effector (1404) will thereby be responsive to longitudinal movement of articulation member (1420). In particular, end effector (1404) will pivot in one direction about pivot (1410) when articulation member (1420) is advanced distally; while end effector (1404) will pivot in the opposite direction about pivot (1410) when articulation member (1420) is retracted proximally. As can be seen in FIGS. 35-36, the distal end of shaft (1402) includes a slot (1440) that is configured to accommodate linkage (1430) when articulation member is retracted to a proximal position. As can also be seen in FIGS. 35-36, a firing beam (1460) may readily flex to transition from shaft (1402) to end effector (1404) when end effector (1404) is articulated in either direction. Articulation joint (1400) may include a curved pathway for firing beam (1460) to readily permit a bend radius for firing beam (1460) when articulation joint (1400) is in an articulated configuration. Such a curved pathway may also be configured to substantially prevent buckling of firing beam (1460) through articulation joint (1400) when firing beam (1460) is actuated while articulation joint (1400) is in an articulated configuration.

In some other versions, linkage (1430) is omitted. For instance, articulation member (1420) may be directly pivotally coupled with end effector (1410) at pivot (1420). Still other suitable ways in which an articulation joint with an offset pivot may be provided will be apparent to those of ordinary skill in the art in view of the teachings herein.

L. Exemplary End Effector with Multi-Position Coupling Feature

Figure 37:
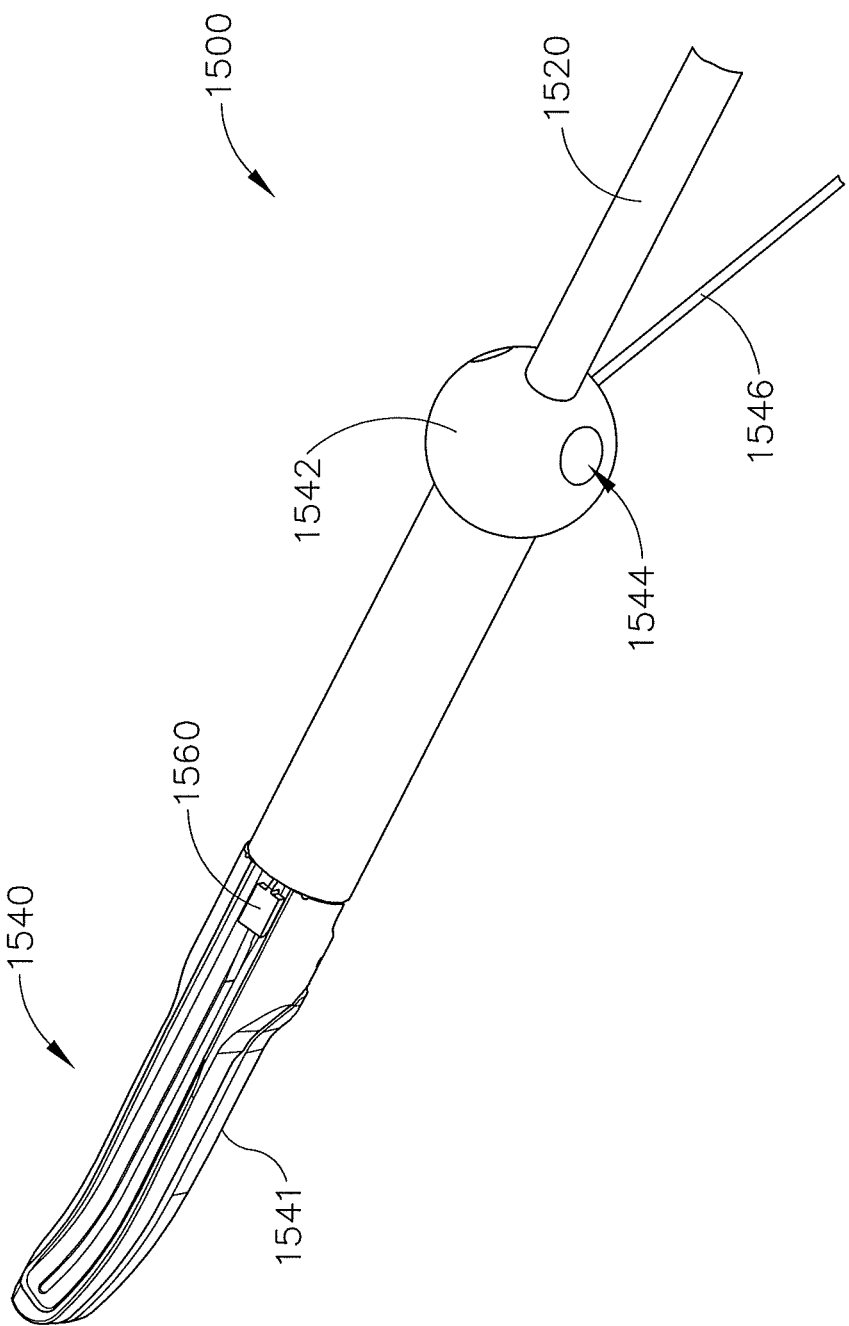
FIG. 37 depicts a perspective view of an exemplary alternative coupling between a shaft and end effector for the device of FIG. 1.

FIG. 37 shows yet another configuration (1500) enabling an end effector (1540) to be selectively articulated at various positions relative to a shaft section (1520). It should be understood that these features may be readily incorporated into electrosurgical instrument (10) described above. In this example, end effector (1540) includes an integral coupling (1542), which presents a plurality of coupling channels (1544) at various positions and orientations. A wire (1546) extends from coupling (1542) and is operable to transmit power from a power source to end effector (1540). Channels (1544) are configured to selectively receive the distal end of shaft section (1520). Shaft section (1520) of this example provides structural support to end effector (1540) when coupling (1542) is secured to shaft section (1520).

In some versions, shaft section (1520) includes one or more features operable to drive firing bar (1560) of end effector (1540) distally and proximally. Various suitable structures that may be used within coupling (1542) and shaft section (1520) to transmit such driving from a component of shaft section (1520) to firing bar (1560) will be apparent to those of ordinary skill in the art in view of the teachings herein. In addition or in the alternative, coupling (1542) may include one or more features operable to drive firing bar (1560), such that shaft section (1520) need not have any moving parts.

In some versions, wire (1546) provides all of the electrical communication for end effector (1540), such that shaft section (1520) is always electrically passive. In some other versions, wire (1546) provides one part of a circuit while shaft section (1520) provides another part of the circuit, such that the circuit is at least substantially completed upon coupling of coupling (1542) with shaft section (1520). By way of example only, channels (1544) and the distal end of shaft section (1520) may include complementary contacts that engage upon coupling of coupling (1542) with shaft section (1520). Various suitable components, features, and configurations that may be used to electrically couple shaft section (1520) with end effector (1540) will be apparent to those of ordinary skill in the art in view of the teachings herein.

In an exemplary use, end effector (1540) and shaft section (1520) are inserted into a patient via separate pathways, and are then joined together after end effector (1540) and shaft section (1520) are both within the patient. For instance, end effector (1540) may be inserted into the patient via one trocar while shaft section (1520) is inserted into the patient via another trocar. As another merely illustrative example, end effector (1540) may be inserted into the patient via one trocar while shaft section (1520) is inserted into the patient percutaneously (e.g., without a trocar). By way of example only, shaft section (1520) may have an outer diameter of approximately 3 mm in such versions. Of course, any other suitable dimensions may be used.

It should be understood that a variety of alternative structures may be used to selectively couple end effector (1540) with shaft section (1520). Some such structures may require end effector (1540) and shaft section (1520) to remain substantially aligned, such that the structures do not permit mounting of end effector (1540) at various angles relative to the longitudinal axis of shaft section (1520). As one merely illustrative alternative, shaft section (1520) may include a tongue feature that is inserted into a hollow interior portion of lower haw (1541) of end effector (1540). Still other suitable structures and configurations for providing selective coupling of an end effector (1540) to a shaft section (1520) within a patient will be apparent to those of ordinary skill in the art in view of the teachings herein.

Similarly, other suitable components, features, configurations, and operabilities for the above described articulation sections (100, 200, 300, 400, 500, 600, 700, 800, 900, 1000, 1100, 1200, 1300, 1400, 1500) will be apparent to those of ordinary skill in the art in view of the teachings herein.

III. Exemplary Articulation Control Configurations

Articulation control (28) may take a variety of forms. By way of example only, articulation control (28) may be configured in accordance with one or more teachings of U.S. patent application Ser. No. 13/235,623, entitled "Control Features for Articulating Surgical Device," filed on even date herewith, published as U.S. Pub. No. 2012/0078243, the disclosure of which is incorporated by reference herein. As another merely illustrative example, articulation control (28) may be configured in accordance with one or more teachings of U.S. patent application Ser. No. 13/235,648, entitled "Control Features for Articulating Surgical Device," filed on even date herewith, published as U.S. Pub. No. 2012/0078244, the disclosure of which is incorporated by reference herein. Furthermore, articulation section may be configured in accordance with the teachings of at least one other of the references cited herein. Various other suitable forms that articulation control (28) may take will be apparent to those of ordinary skill in the art in view of the teachings herein.

IV. Other Exemplary Features

It should be understood that any of the versions of electrosurgical instrument (10) described herein may include various other features in addition to or in lieu of those described above. Several examples of such other features are described below, while other features will be apparent to those of ordinary skill in the art in view of the teachings herein.

A. Exemplary Alternative Cutting Member Actuation

In examples described above, a blade (64) is advanced distally through end effector (40) by advancing firing bar (60) distally. In the example depicted in FIGS. 38A-38B, a blade (1664) is advanced distally by retracting a firing band (1660) proximally. In this example, blade (1664) is distally presented by a blade member (1668), which includes upper flange members (1662) and which is secured to a distal end of firing band (1660). Blade member (1668) travels longitudinally along a slot (1646) formed in a lower jaw (1644) of an end effector assembly. Blade member (1668) further includes lower flange members (not shown) that are disposed beneath lower jaw (1644). By way of example only, lower jaw (44) of electrosurgical instrument (10) may be readily modified to include the features of lower jaw (1644) described in this example.

The distal end of lower jaw (1644) includes a post (1670). Firing band (1660) is wrapped around post (1670) such that post (1670) redirects the longitudinal motion of firing band (1660) by approximately 180°. Firing band (1660) has sufficient flexibility to provide such motion, yet also has enough tensile strength to bear significant loads on blade member (1668) as blade (1664) severs tissue. In some versions, post (1670) includes a bushing or bearing that is configured to facilitate movement of firing band (1660) about post (1670). As can be seen from the transition between FIG. 38A and FIG. 38B, blade member (1668) advances distally along channel (1646) from a proximal position to a distal position in response to proximal movement of firing band (1660). In some versions, firing band (1660) may also be advanced distally to return blade member (1668) from the distal position to the proximal position. For instance, lower jaw (1644) may include guide channels that guide firing band (1660) and prevent firing band (1660) from buckling as firing band (1660) is advanced distally. Various suitable ways in which firing band (1660) may be translated distally and/or proximally will be apparent to those of ordinary skill in the art in view of the teachings herein. It should also be understood that, in some versions, advancing blade member (1668) distally by pulling firing band (1660) proximally when the end effector is articulated may be relatively easier than advancing a blade member (1668) would otherwise be if a firing beam (60) were advanced distally to advance a blade member with an end effector (40) articulated. In other words, firing band (1660) may facilitate configurations with articulation angles that are greater than those provided by devices that use distally advanced firing beams (60).

It should be understood that firing band (1660) may be used in versions of electrosurgical device (10) that lack an articulation section (36). It should also be understood that, just like various other components described herein, firing band (1660) may be used in a variety of other types of devices beyond electrosurgical devices, including but not limited to endocutter surgical stapling devices. Other suitable implementations will be apparent to those of ordinary skill in the art in view of the teachings herein.

B. Exemplary Dual Pivoting Jaws

Figure 39A:
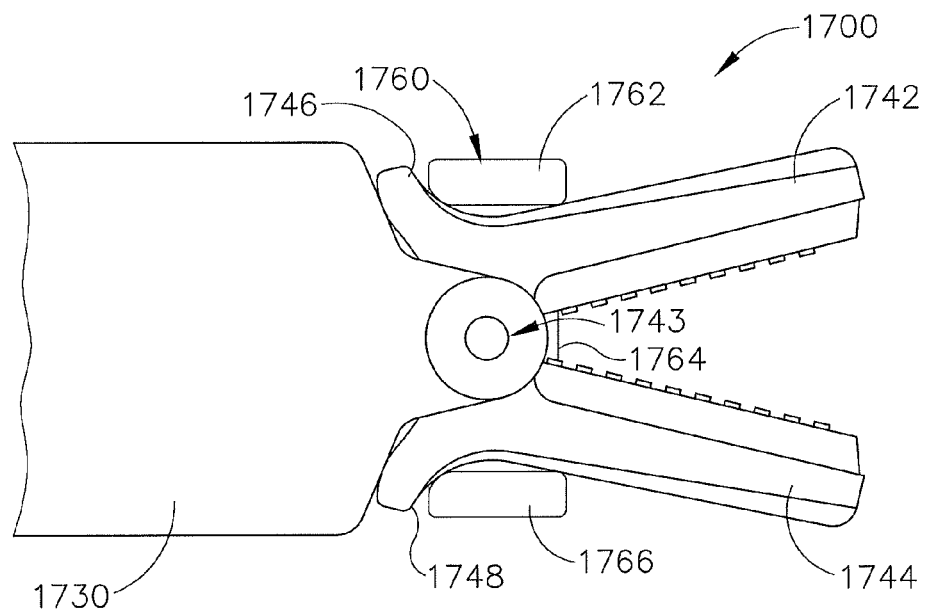
FIG. 39A depicts a side elevational view of another exemplary alternative end effector for incorporation into the device of FIG. 1, with a cutting member positioned at a proximal location.
Figure 39B:
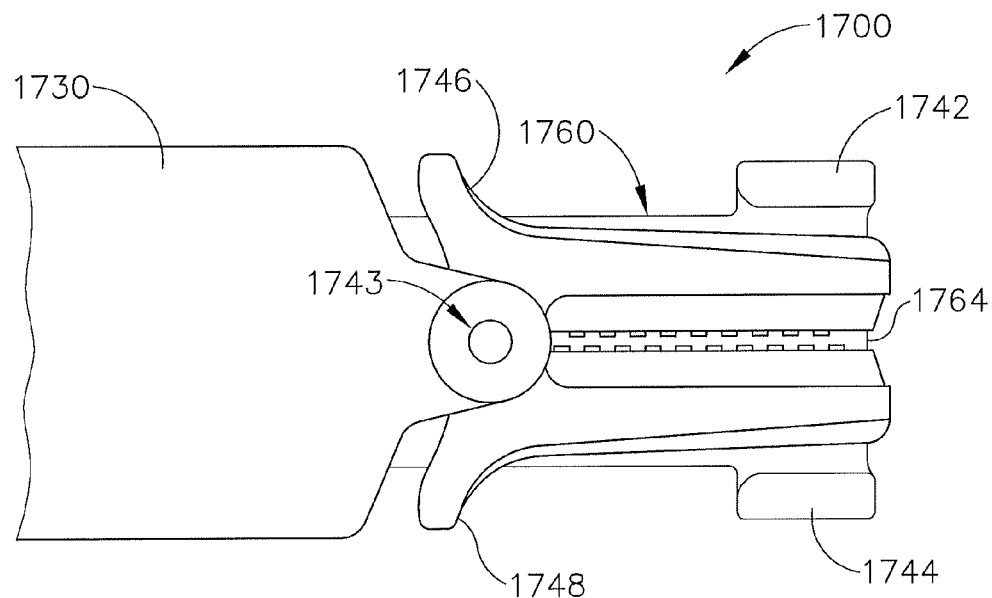
FIG. 39B depicts a side elevational view of the end effector of FIG. 39A, with the cutting member positioned at a distal location.

FIGS. 39A-39B show a dual pivoting jaw assembly (1700) that may be incorporated into any version of electrosurgical device (10) described herein. In the example depicted in FIGS. 1-4, lower jaw (44) remains substantially stationary relative to pivotal coupling (43), such that only upper jaw (42) moves when jaws (42, 44) are opened and closed. By contrast, in the jaw assembly (1700) of FIGS. 39A-39B, both an upper jaw (1742) and a lower jaw (1744) pivot relative to pivotal coupling (1743). Pivotal coupling (1743) is disposed at the distal end of a shaft assembly (1730). Like firing beam (60), a firing beam (1760) in this example includes a sharp distal blade (1764), an upper flange (1762), and a lower flange (1766). Also like firing beam (60), firing beam (1760) is operable to translate longitudinally relative to shaft assembly (30).

Each jaw (1742, 1744) includes a respective proximal projection (1746, 1748). Proximal projection (1746) of upper jaw (1742) is configured to interact with upper flange (1762); while proximal projection (1748) of lower jaw (1744) is configured to interact with lower flange (1766). In particular, as shown in FIG. 39A, upper flange (1762) cams against proximal projection (1746) to place upper jaw (1742) in an open position when firing beam (1760) is in a proximal position Likewise, lower flange (1766) cams against proximal projection (1748) to place lower jaw (1744) in an open position when firing beam (1760) is in a proximal position. As firing beam (1760) is translated distally, flanges (1762, 1764) cam against the exteriors of jaws (1742, 1744) to close jaws (1742, 1744) together simultaneously. It should be understood that enabling both jaws (1742, 1744) to pivot away from the longitudinal axis defined by jaw assembly (1700) may provide better visibility of a surgical site regardless of the rotational orientation of jaw assembly (1700) as compared to visibility provided with jaw assemblies where the pivotal position of one jaw is fixed.

It should be understood that dual pivoting jaw assembly (1700) may be used in versions of electrosurgical device (10) that lack an articulation section (36). It should also be understood that, just like various other components described herein, dual pivoting jaw assembly (1700) may be used in a variety of other types of devices beyond electrosurgical devices, including but not limited to endocutter surgical stapling devices. Other suitable implementations will be apparent to those of ordinary skill in the art in view of the teachings herein.

C. Exemplary Wire Tensioning Feature

Figure 40:
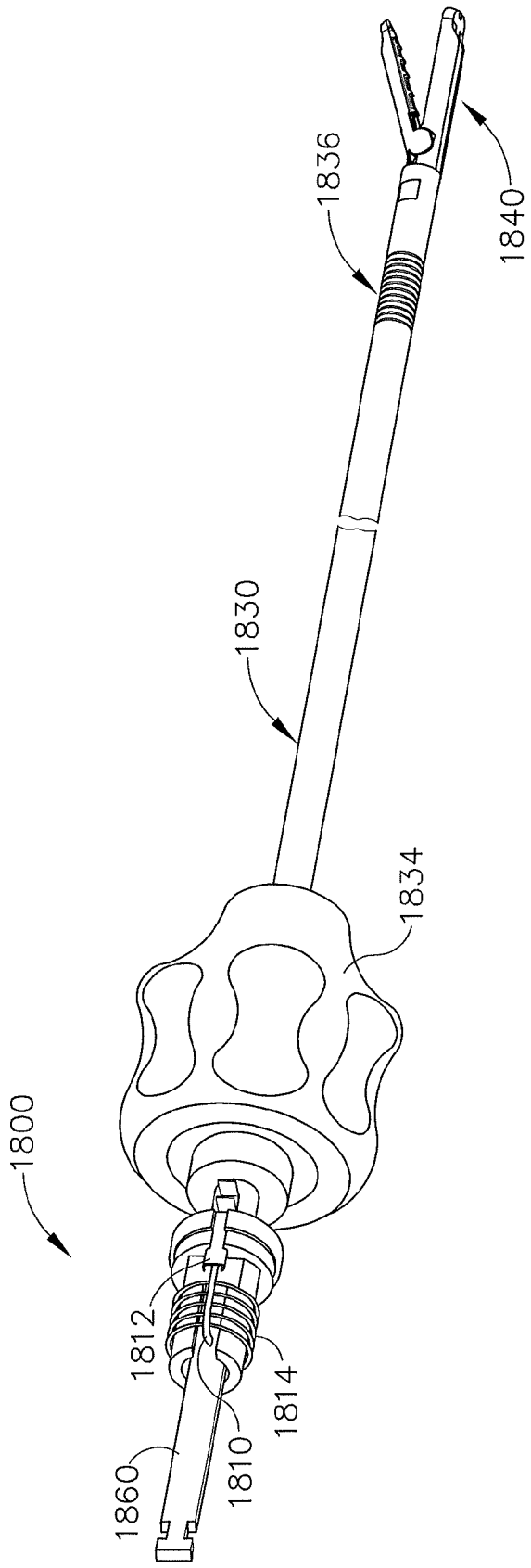
FIG. 40 depicts a perspective view of an exemplary shaft assembly with wire tensioning feature, for incorporation into the device of FIG. 1.
Figure 41:
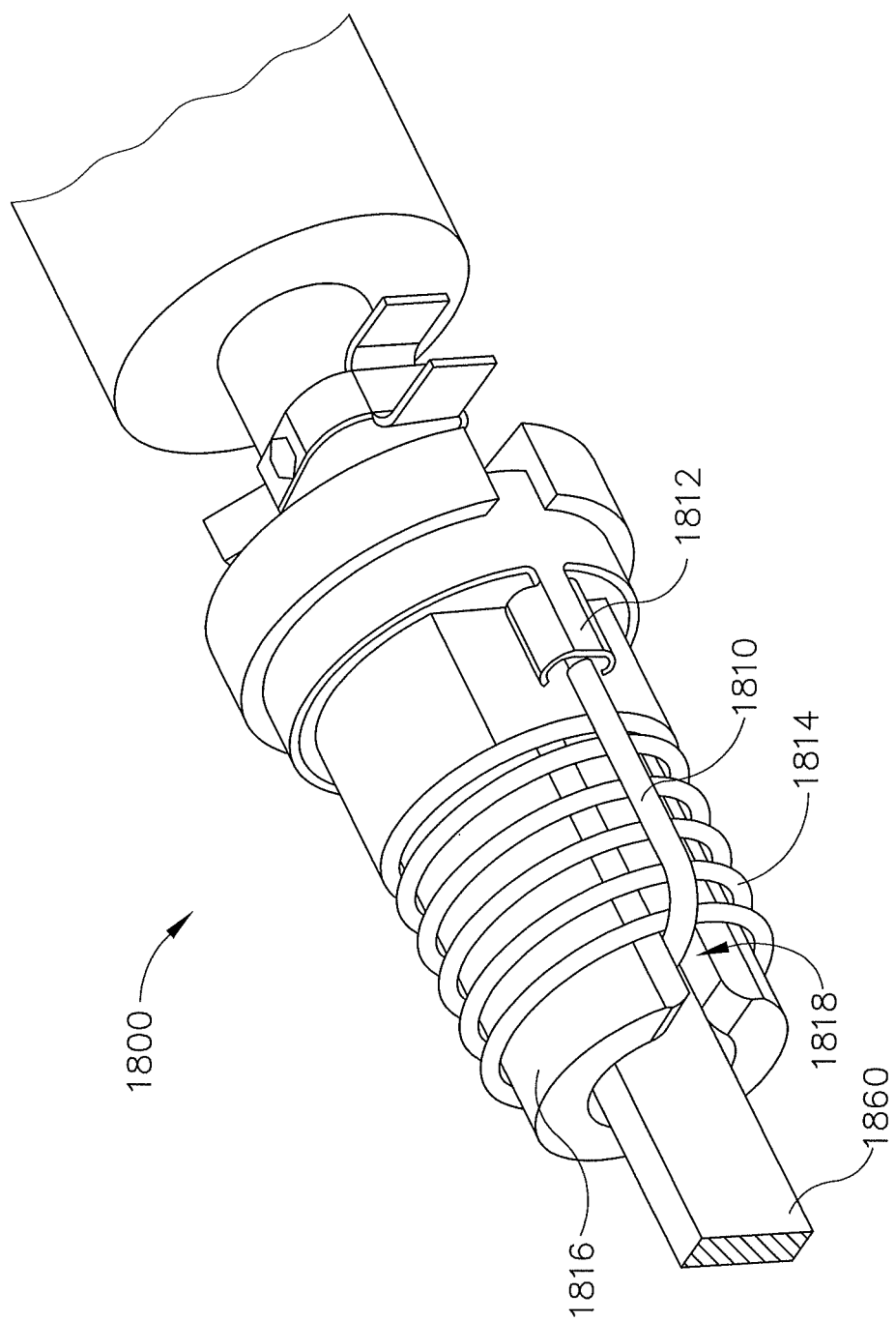
FIG. 41 depicts a perspective view of the tensioning feature of FIG. 40.

In one or more of the examples described herein, a wire may pass through an articulation section in a way that requires the wire to extend its effective length or in a way that otherwise pulls the wire when an articulating section through which the wire passes is articulated. Thus, it may be desirable in some instances to allow a wire to be pulled through a shaft and through an articulation section while the articulation section is in a bent/articulated configuration. However, it may also be desirable to prevent such a wire from bunching up, getting pinched, or interfering with other components when the articulation section is in a substantially straight configuration (when the wire does not need to be as effectively long). FIGS. 40-41 show one merely exemplary wire tensioning assembly (1800) that may be used to maintain tension in a wire (1810) while also allowing wire (1810) to increase its effective length when an articulation section (1836) is articulated to a bent configuration. In this example, tensioning assembly (1800) is located proximal to a rotation knob (1834) at the proximal end of a shaft assembly (1830). The distal end of shaft assembly (1830) includes an articulation section (1836) and an end effector (1840). Knob (1834) is operable to rotate shaft assembly (1830) relative to a handpiece or other type of body, about the longitudinal axis defined by shaft assembly (1830). Articulation section (1836) may be constructed and operable in accordance with any articulation section described herein. Alternatively, articulation section (1836) may have any other suitable configuration. Similarly, end effector (1840) may be constructed and operable in accordance with any end effector described herein; or may have any other suitable configuration.

Wire (1810) is configured to deliver power from a power source to end effector (1840), in accordance with the teachings herein or otherwise. Thus, a distal end of wire (1810) is coupled with end effector (1840), distal to articulation section (1836). Wire (1810) extends proximally through shaft assembly (1830). In some versions, shaft assembly (1830) includes an internal component that provides a groove, passageway, or other feature that substantially contains wire (1840) while allowing wire (1840) to translate within shaft assembly (1830).

Wire tensioning assembly (1800) includes a conductive anchor (1812) and a coil spring (1814) coupled with a body portion (1816). Wire (1810) passes through a slot (1818) formed in body portion (1816) and is redirected approximately 180°, such that the proximal end of wire (1810) is secured to conductive anchor (1812). Conductive anchor (1812) couples with a complementary feature in a handpiece or other type of body portion, to communicate power from the power source to wire (1810). Coil spring (1814) resiliently bears proximally on wire (1810), as best seen in FIG. 41, to keep wire (1810) in tension. When additional length of wire (1810) is needed in response to bending of articulation section (1836), coil spring (1814) compresses and wire (1810) travels through slot (1818) to provide such additional length. When the additional length of wire (1810) is no longer needed (e.g., when articulation section (1836) is straightened), coil spring (1814) expands and pulls wire (1810) through slot (1818) to take up slack. As can also be seen in FIGS. 40-41, firing beam (1860) passes through body portion (1816) and reciprocates therethrough without interference with wire (1810). Other suitable components, features, and configurations that may be used for tensioning assembly (1800) will be apparent to those of ordinary skill in the art in view of the teachings herein.

D. Exemplary Alternative Cutting Member

Figure 42B:
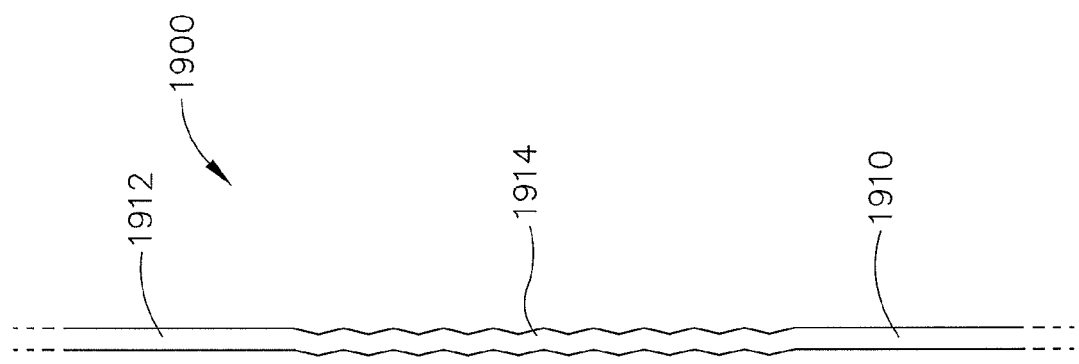
FIG. 42B depicts a top plan view of the crimped cutting member of FIG. 42A, in a substantially straight configuration.
Figure 42A:
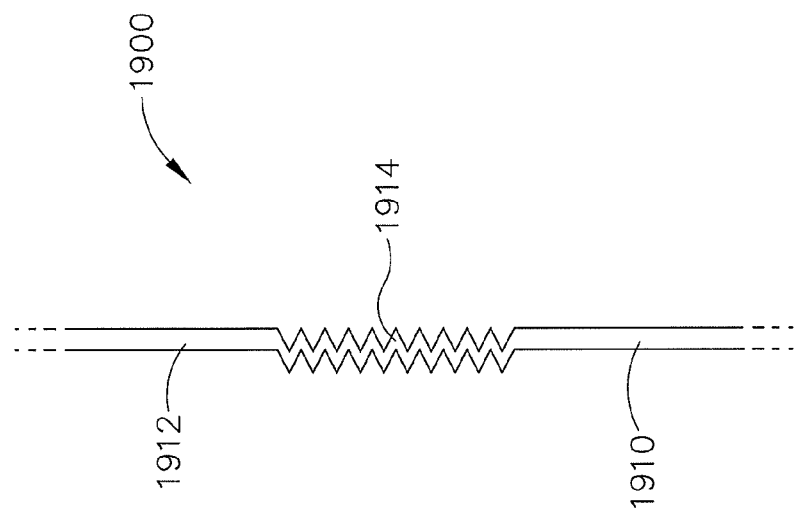
FIG. 42A depicts a top plan view of an exemplary crimped cutting member for incorporation into the device of FIG. 1, with the cutting member in a substantially crimped configuration.
Figure 43:
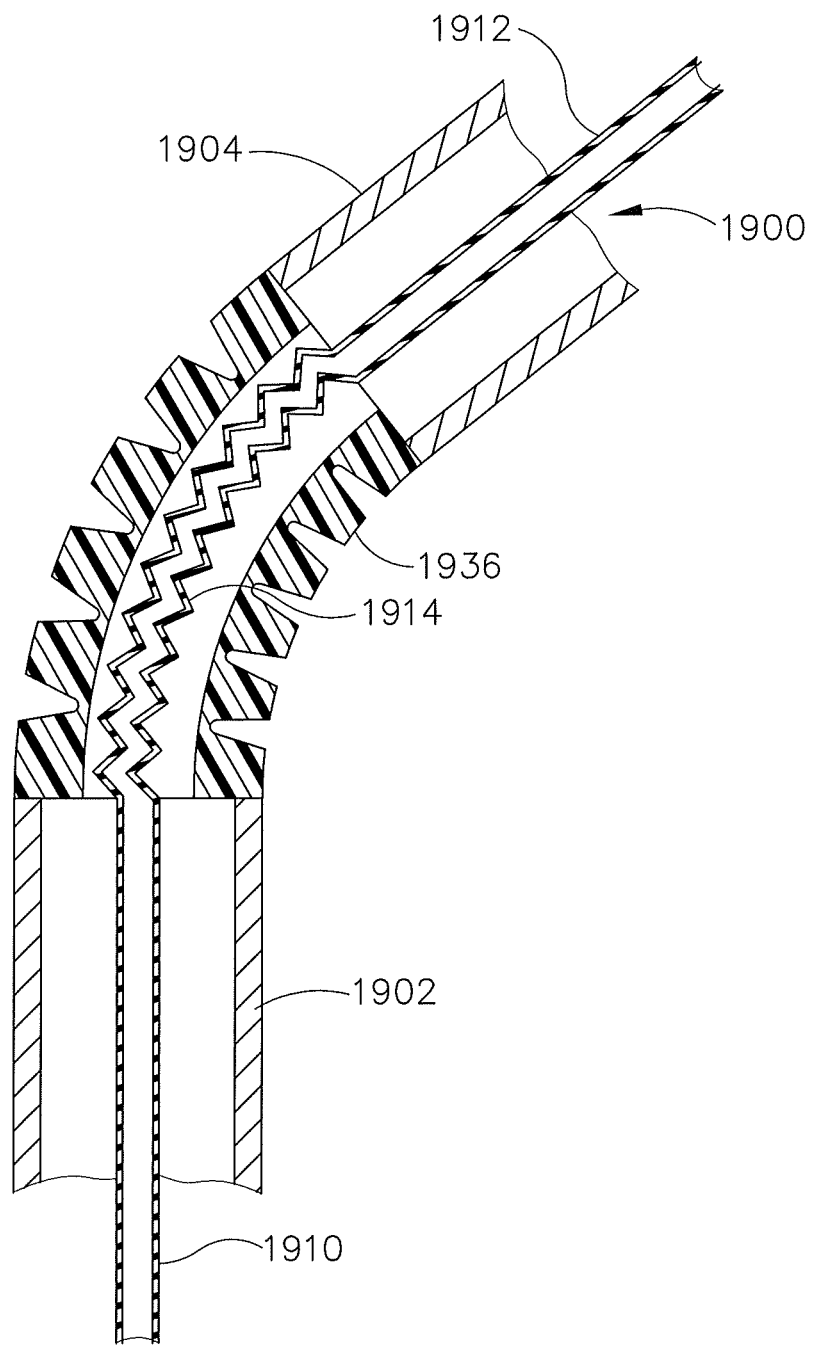
FIG. 43 depicts a cross-sectional view of an exemplary articulating section for incorporation into the device of FIG. 1, including the crimped cutting member of FIG. 42A.

FIGS. 42A-43 show an exemplary crimped firing beam (1900) that may be used in place of any firing beam described herein. In this example, firing beam (1900) includes a proximal straight section (1910), a distal straight section (1912), and a crimped section (1914) positioned between straight sections (1910, 1912). Crimped section (1914) is configured to enable firing beam (1900) to transition between a compressed configuration as shown in FIG. 42A and an extended configuration as shown in FIG. 42B. Crimped section (1914) is resiliently biased to assume the compressed configuration in this example. As shown in FIG. 43, crimped section (1914) is positioned to extend through an articulation section (1936), which is positioned between a rigid shaft section (1902) and an end effector (1904). It should be understood that articulation section (1936), rigid shaft section (1902), and end effector (1904) may be constructed and operable in accordance with any of the teachings of such components herein.

As noted above in the discussion of wire (1810) and wire tensioning assembly (1800), the length demands of components passing through an articulation section (1936) may change based on the degree of articulation of the articulation section (1936). For instance, when articulation section (1936) is in a bent configuration, this may require additional length from a firing beam (1900) that passes through articulation section (1936). Crimped section (1936) may provide this additional length by extending when articulation section (1936) is bent. Crimped section (1936) may contract when articulation section (1936) is straightened. It should be understood that crimped section may be configured to transmit longitudinal loads just as well when it is expanded (FIG. 42B) as when it is compressed (FIG. 42A), to enable satisfactory closure of jaws of end effector (1904) and to further enable severing of tissue clamped between jaws of end effector (1904) by a blade at the distal end of straight section (1912). Thus, the blade at the distal end of straight section (1912) will ultimately travel the same distance through end effector (1904) regardless of whether articulation section (1936) is in a bent configuration or a substantially straight configuration.

It should be understood that, just like various other components described herein, crimped firing beam (1900) may be used in a variety of other types of devices beyond electrosurgical devices, including but not limited to endocutter surgical stapling devices. Other suitable implementations will be apparent to those of ordinary skill in the art in view of the teachings herein.

Various examples described herein include components that extend through an articulation section to an end effector and that may be formed of electrically conductive materials, including but not limited to various firing beams, firing bands, support beams, articulation beams, articulation cables, etc. Any such components may be used to provide electrical communication to a component of an end effector. By way of example only such components may be used to communicate power to the end effector from a power source, to provide a ground return path, to communicate signals to or from the end effector, etc. Of course, such components may also include appropriate insulation as needed or desired. Various suitable ways in which such components may be used to communicate power, signals, etc. through an articulation section will be apparent to those of ordinary skill in the art in view of the teachings herein.

It should be understood that any of the devices herein may also include one or more of the various features disclosed in U.S. patent application Ser. No. 13/235,623, entitled "Control Features for Articulating Surgical Device," filed on even date herewith, published as U.S. Pub. No. 2012/0078243, the disclosure of which is incorporated by reference herein; U.S. patent application Ser. No. 13/235,648, entitled "Control Features for Articulating Surgical Device," filed on even date herewith, published as U.S. Pub. No. 2012/0078244, the disclosure of which is incorporated by reference herein; and/or U.S. patent application Ser. No. 13/235,660, entitled "Articulation Joint Features for Articulating Surgical Device," filed on even date herewith, published as U.S. Pub. No. 2012/0078247, the disclosure of which is incorporated by reference herein.

It should also be understood that any of the devices described herein may be modified to include a motor or other electrically powered device to drive an otherwise manually moved component. Various examples of such modifications are described in U.S. patent application Ser. No. 13/151,481, entitled "Motor Driven Electrosurgical Device with Mechanical and Electrical Feedback," filed Jun. 2, 1011, now U.S. Pat. No. 9,161,803 issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

Furthermore, it should be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

VI. Miscellaneous

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An electrosurgical device, comprising:
(a) a body;
(b) an end effector comprising:
 (i) a first jaw, and
 (ii) a second jaw,
 wherein the first jaw is movable toward the second jaw to clamp tissue between the first and second jaw,
 wherein at least one of the jaws comprises at least one electrode,
 wherein the at least one electrode is operable to deliver RF energy to tissue clamped between the first and second jaw;
(c) a cutting member operable to cut tissue clamped between the first jaw and the second jaw; and
(d) a shaft extending between the body and the end effector, wherein the shaft defines a longitudinal axis, wherein the shaft includes an articulation section, wherein the articulation section is operable to selective position the end effector at non-parallel positions relative to the longitudinal axis of the shaft;
wherein the articulation section is formed by a plurality of segments, wherein the segments include electrical contacts configured to provide electrical communication through the articulation section, wherein the articulation section further comprises one or more resilient members biased to urge the contacts apart from each other.

2. The electrosurgical device of claim 1, wherein the plurality of segments comprises a plurality of beads, wherein the beads are positioned adjacent to each other.

3. The electrosurgical device of claim 1, wherein the plurality of segments include complementary posts and passages, wherein the post of each segment is disposed in the passage of another segment such that the beads are pivotally linked together by the posts.

4. The electrosurgical device of claim 1, wherein the plurality of segments further comprise a plurality of interlocking segments, wherein the interlocking segments are operable to selectively lock the articulation section in an articulated configuration.

5. The electrosurgical device of claim 1, wherein the articulation section has a configuration that is asymmetric about a longitudinal axis defined by the articulation section when the articulation section is in a straight position.

6. The electrosurgical device of claim 1, wherein the articulation section further comprises an elastic member preformed to assume a bent configuration.

7. The electrosurgical device of claim 6, wherein the articulation section comprises a movable beam, wherein the movable beam is retractable to substantially straighten the elastic member.

8. The electrosurgical device of claim 1, wherein the articulation section comprises:
(i) an elastic member preformed to assume a bent configuration, and
(ii) a rod movable within the elastic member to substantially straighten the elastic member based on the longitudinal position of the rod within the elastic member.

9. The electrosurgical device of claim 1, wherein the articulation section is preformed to assume a non-straight configuration, wherein the cutting member comprises a beaded linkage extending through the articulation section, wherein the beaded linkage is configured to transfer longitudinal motion through the articulation section.

10. The electrosurgical device of claim 1, wherein the articulation section comprises an offset pivot disposed lateral to and perpendicular to the longitudinal axis of the shaft, wherein the end effector is pivotable about the offset pivot.

11. The electrosurgical device of claim 1, wherein the end effector is removable from the shaft, wherein the end effector is configured to selectively couple with the shaft at two or more selected angles relative to the shaft.

12. The electrosurgical device of claim 1, wherein the cutting member includes a crimped section.

* * * * *